US00RE45509E

(19) United States
(12) Reissued Patent
Foley et al.

(10) Patent Number: US RE45,509 E
(45) Date of Reissued Patent: May 5, 2015

(54) PERCUTANEOUS REGISTRATION APPARATUS AND METHOD FOR USE IN COMPUTER-ASSISTED SURGICAL NAVIGATION

(71) Applicant: Medtronic Navigation, Inc., Louisville, CO (US)

(72) Inventors: Kevin T. Foley, Germantown, TN (US); John B. Clayton, Superior, CO (US); Anthony J. Melkent, Germantown, TN (US); Michael C. Sherman, Memphis, TN (US)

(73) Assignee: Medtronic Navigation, Inc., Louisville, CO (US)

(21) Appl. No.: 13/919,648

(22) Filed: Jun. 17, 2013

Related U.S. Patent Documents

Reissue of:
(64) Patent No.: 6,226,548
Issued: May 1, 2001
Appl. No.: 09/148,498
Filed: Sep. 4, 1998

U.S. Applications:
(63) Continuation of application No. 13/036,939, filed on Feb. 28, 2011, now Pat. No. Re. 44,305, which is a continuation of application No. 11/451,595, filed on Jun. 12, 2006, (Continued)

(51) Int. Cl.
*A61B 5/05* (2006.01)
*A61B 17/70* (2006.01)

(52) U.S. Cl.
CPC ..... *A61B 17/70* (2013.01)

(58) Field of Classification Search
USPC ..... 600/426
See application file for complete search history.

(56) References Cited

U.S. PATENT DOCUMENTS 3,821,469 A 6/1974 Whetstone et al.
3,983,474 A 9/1976 Kuipers (Continued)

FOREIGN PATENT DOCUMENTS

DE 197 15 202 A1 1/1997
EP 0 018 166 A1 4/1980

(Continued)

OTHER PUBLICATIONS

Weinstein, et al., Spinal Pedicle Fixation: Reliability and Validity of Roentgenogram—Based Assessment and Surgical Factors on Successful Screw Placement, *Spine*, vol. 13, No. 9, 1988, pp. 1012-1018.

(Continued)

*Primary Examiner* — George Manuel
(74) *Attorney, Agent, or Firm* — Harness, Dickey

(57) ABSTRACT

An apparatus and procedures for percutaneous placement of surgical implants and instruments such as, for example, screws, rods, wires and plates into various body parts using image guided surgery. The invention includes an apparatus for use with a surgical navigation system, an attaching device rigidly connected to a body part, such as the spinous process of a vertebrae, with an identification superstructure rigidly but removably connected to the attaching device. This identification superstructure, for example, is a reference arc and fiducial array which accomplishes the function of identifying the location of the superstructure, and, therefore, the body part to which it is fixed, during imaging by CAT scan or MRI, and later during medical procedures.

25 Claims, 19 Drawing Sheets

Related U.S. Application Data now Pat. No. Re. 42,226, which is a continuation of application No. 10/423,332, filed on Apr. 24, 2003, now Pat. No. Re. 39,133, which is an application for the reissue of Pat. No. 6,226,548.

(60) Provisional application No. 60/059,915, filed on Sep. 24, 1997.

(56) References Cited

U.S. PATENT DOCUMENTS

| | | | | |
|---|---|---|---|---|
| 4,058,114 | A | 11/1977 | Soldner | |
| 4,209,254 | A | 6/1980 | Reymond et al. | |
| 4,259,725 | A | 3/1981 | Andrews et al. | |
| 4,262,306 | A | 4/1981 | Renner | |
| 4,341,220 | A | 7/1982 | Perry | |
| 4,396,945 | A | 8/1983 | DiMatteo et al. | |
| 4,398,540 | A | 8/1983 | Takemura et al. | |
| 4,419,012 | A | 12/1983 | Stephenson et al. | |
| 4,457,311 | A | 7/1984 | Sorenson et al. | |
| 4,543,959 | A | 10/1985 | Sepponen | |
| 4,583,538 | A | 4/1986 | Onik et al. | |
| 4,592,352 | A | 6/1986 | Patil | |
| 4,602,622 | A | 7/1986 | Bär et al. | |
| 4,608,977 | A | 9/1986 | Brown | |
| 4,638,798 | A | 1/1987 | Shelden et al. | |
| 4,649,504 | A | 3/1987 | Krouglicof et al. | |
| 4,686,997 | A | 8/1987 | Oloff et al. | |
| 4,701,049 | A | 10/1987 | Beckman et al. | |
| 4,705,395 | A | 11/1987 | Hageniers | |
| 4,705,401 | A | 11/1987 | Addleman et al. | |
| 4,706,665 | A | 11/1987 | Gouda | |
| 4,723,544 | A | 2/1988 | Moore et al. | |
| 4,733,661 | A | 3/1988 | Palestrant | |
| 4,737,921 | A | 4/1988 | Goldwasser et al. | |
| 4,750,487 | A | 6/1988 | Zanetti | |
| 4,771,787 | A | 9/1988 | Wurster et al. | |
| 4,779,212 | A | 10/1988 | Levy | |
| 4,782,239 | A | 11/1988 | Hirose et al. | |
| 4,788,481 | A | 11/1988 | Niwa | |
| 4,791,934 | A | 12/1988 | Brunnett | |
| 4,793,355 | A | 12/1988 | Crum et al. | |
| 4,805,615 | A | 2/1989 | Carol | |
| 4,809,694 | A | 3/1989 | Ferrara | |
| 4,836,778 | A | 6/1989 | Baumrind et al. | |
| 4,841,967 | A | 6/1989 | Chang et al. | |
| 4,875,478 | A | 10/1989 | Chen | |
| 4,896,673 | A | 1/1990 | Rose et al. | |
| 4,931,056 | A | 6/1990 | Ghajar et al. | |
| 4,943,296 | A | 7/1990 | Funakubo et al. | |
| 4,945,914 | A | 8/1990 | Allen | |
| 4,955,891 | A | 9/1990 | Carol | |
| 4,991,579 | A | 2/1991 | Allen | |
| 5,016,639 | A | 5/1991 | Allen | 600/414 |
| 5,047,036 | A | 9/1991 | Koutrouvelis | |
| 5,078,140 | A | 1/1992 | Kwoh | |
| 5,080,662 | A | 1/1992 | Paul | |
| 5,094,241 | A | 3/1992 | Allen | |
| 5,097,839 | A | 3/1992 | Allen | |
| 5,119,817 | A | 6/1992 | Allen | |
| 5,142,930 | A | 9/1992 | Allen et al. | |
| 5,178,164 | A | 1/1993 | Allen | |
| 5,186,174 | A | 2/1993 | Schlöndorff et al. | |
| 5,198,877 | A | 3/1993 | Schulz | |
| 5,211,164 | A | 5/1993 | Allen | |
| 5,222,499 | A | 6/1993 | Allen et al. | |
| 5,230,338 | A | 7/1993 | Allen et al. | |
| 5,230,623 | A | 7/1993 | Guthrie et al. | |
| 5,249,581 | A | 10/1993 | Horbal et al. | |
| 5,251,127 | A | 10/1993 | Raab | |
| 5,257,998 | A | 11/1993 | Ota et al. | |
| 5,279,309 | A | 1/1994 | Taylor et al. | |
| 5,295,200 | A | 3/1994 | Boyer | |
| 5,295,483 | A | 3/1994 | Nowacki et al. | |
| 5,299,288 | A | 3/1994 | Glassman et al. | |
| 5,305,203 | A | 4/1994 | Raab | |
| 5,309,913 | A | 5/1994 | Kormos et al. | |
| 5,371,778 | A | 12/1994 | Yanof et al. | |
| 5,383,454 | A | 1/1995 | Bucholz | |
| 5,389,101 | A | 2/1995 | Heilbrun et al. | |
| 5,402,801 | A | 4/1995 | Taylor | |
| 5,447,154 | A | 9/1995 | Cinquin et al. | |
| 5,483,961 | A | 1/1996 | Kelly et al. | |
| 5,494,034 | A | 2/1996 | Schlöndorff et al. | |
| 5,515,160 | A | 5/1996 | Schulz et al. | |
| 5,517,990 | A | 5/1996 | Kalfas et al. | |
| 5,526,576 | A | 6/1996 | Fuchs et al. | |
| 5,551,429 | A | 9/1996 | Fitzpatrick et al. | |
| 5,572,999 | A | 11/1996 | Funda et al. | |
| 5,603,318 | A | 2/1997 | Heilbrun et al. | |
| 5,603,328 | A | 2/1997 | Zucker et al. | |
| 5,617,857 | A | 4/1997 | Chader et al. | |
| 5,622,170 | A | 4/1997 | Schulz | |
| 5,630,431 | A | 5/1997 | Taylor | |
| 5,638,819 | A | 6/1997 | Manwaring et al. | |
| 5,662,111 | A | 9/1997 | Cosman | |
| 5,676,673 | A | 10/1997 | Ferre et al. | |
| 5,748,767 | A | 5/1998 | Raab | |
| 5,749,362 | A | 5/1998 | Funda et al. | |
| 5,755,725 | A | 5/1998 | Druais | |
| RE35,816 | E | 6/1998 | Schulz | |
| 5,772,594 | A * | 6/1998 | Barrick | 600/407 |
| 5,795,294 | A | 8/1998 | Luber et al. | |
| 5,823,958 | A | 10/1998 | Truppe | |
| 5,834,759 | A | 11/1998 | Glossop | |
| 5,836,954 | A | 11/1998 | Heilbrun et al. | |
| 5,848,967 | A | 12/1998 | Cosman | |
| 5,851,183 | A | 12/1998 | Bucholz | |
| 5,868,675 | A | 2/1999 | Henrion et al. | |
| 5,871,445 | A | 2/1999 | Bucholz | |
| 5,891,034 | A * | 4/1999 | Bucholz | 600/426 |
| 6,006,126 | A * | 12/1999 | Cosman | 600/426 |

FOREIGN PATENT DOCUMENTS

| | | |
|---|---|---|
| EP | 0 359 773 B1 | 5/1988 |
| EP | 0 326 768 A2 | 12/1988 |
| EP | 0 427 358 A1 | 10/1990 |
| EP | 0 501 993 B1 | 11/1990 |
| EP | 0 456 103 A2 | 5/1991 |
| EP | 0 469 966 A1 | 7/1991 |
| WO | WO 88/09151 | 12/1988 |
| WO | WO 91/07726 | 5/1991 |
| WO | WO 92/06645 | 4/1992 |
| WO | WO 94/23647 | 10/1994 |
| WO | WO 94/24933 | 11/1994 |
| WO | WO 96/11624 | 4/1995 |
| WO | WO 96/11624 | 4/1996 |
| WO | WO 96/32059 | 10/1996 |
| WO | WO 97/40764 | 11/1997 |

OTHER PUBLICATIONS

Kelly, The NeuroStation System for Image-Guided, Frameless Stereotaxy, *Neurosugery*, vol. 37, No. 2, Aug. 1995, pp. 348-350.

Vector Vision: The Power of Surgical Tracking, *BrainLab*, 1997.

J.F. Mallet, et al., Post-Laminectomy Cervical-Thoracic Kyphosis in a Patient with Von Recklinghausen's Disease, *Spinal Frontiers*, vol. Three, Issue One, Apr. 1996, pp. 1-15.

Bucholz, et al., Image-Guided Surgical Techniques for Infections and Trauma of the Central Nervous Systems, *Neurosurgery Clinics of North America*, vol. 7, No. 2, Apr. 1996, pp. 187-200.

Foley, et al., Image-guided Intraoperative Spinal Localization, *Intraoperative Neuroprotection: Monitoring*, Part Three, 1996, pp. 325-340.

Mazier, et al., Computer Assisted Interventionist Imaging: Application to the Vertebral Column Surgery, *Annual International Conference of the IEEE Engineering in Medicine and Biology Society*, vol. 12, No. 1, 1990, pp. 0430-0431.

Lavallée, et al., Computer Assisted Medical Interventions, *NATO ASI Series*, vol. F 60, 1990, pp. 301-312.

(56) References Cited

OTHER PUBLICATIONS

Adams et al., Computer-Assisted Surgery, *IEEE Computer Graphics & Applications* , May 1990, pp. 43-51.
3-D Digitizer Captures the World, *BYTE*, Oct. 1990, p. 43.
Reinhardt, et al., Interactive Sonar-Operated Device for Stereotactic and Open Surgery, *Proceedings of the Xth Meeting of the World Society for Stereotactic and Functional Neurosurgery*, Maebashi, Japan, Oct. 1989, pp. 393-397.
Kato, et al., A frameless, armless navigational system fo computer-assisted neurosurgery, *J. Neurosurg 74*, 1991, pp. 845-849.
Smith et al., Multimodality Image Analysis and Display Methods for Improved Tumor Localization in Stereotatic Neurosurgery, *Proceedings of the Annual International Conference of the IEEE Engineering in Medicine and Biology Society*, vol. 13, 1991, p. 0210.
Sautot et al., Computer Assisted Spine Surgery: a first step toward clinical application in orthopaedics, *IEEE*, 1992, p. 1071-1072.
Cinquin, et al., GOR: Image Guided Operating Robot. Methodology, Application, *IEEE EMBS*, Paris 1992, pp. 1-2.
Alignment Procedure for the PixSys Two-Emitter Offset Probe for the SAC GP-8-3d Sonic Digitizer, *PixSys*, Jul. 2, 1992, pp. 1-4.
Smith, et al., Computer Methods for Improved Diagnostic Image Display Applied to Stereotatic Neurosurgery, *Automedica*, 1992, vol. 14, pp. 371-382.
Reinhardt, Neuronavigation: A Ten-Year Review, *Neurosurgery*, 1993, pp. 329-341.
Bucholz, et al., Intraoperative localization using a three dimensional optical digitizer, *SPIE*vol. 1894, Jan. 17, 1993, pp. 312-322.
Smith, et al., The Neurostation™-A Highly Accurate, Minimally Invasive Solution to Frameless Stereotactic Neurosurgery, *Computerized Medical Imaging and Graphics*, vol. 18, 1994, pp. 247-256.
Bucholz, et al., Halo vest versus spinal fusion for cervical injury: evidence from an outcome study, *J. Neurosurg.*, vol. 70, pp. 884-892.
Awwad, et al., Post-traumatic Spinal Synovial Cyst with Spondylolysis: CT Features, *Journal of Computer Assisted Tomography*, vol. 13, No. 2, 1989, pp. 334-337.

* cited by examiner

PERCUTANEOUS REGISTRATION APPARATUS AND METHOD FOR USE IN COMPUTER-ASSISTED SURGICAL NAVIGATION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*This application is a reissue of U.S. Pat. No. 6,226,548 issued on May 1, 2001 and also claims benefit under 35 U.S.C. §120 as a reissue continuation of U.S. patent application Ser. No. 13/036,939, filed on Feb. 28, 2011, now U.S. Pat. No. Re. 44,305, issued on Jun. 18, 2013; which also claims benefit under 35 U.S.C. §120 as a continuation of U.S. patent application Ser. No. 11/451,594, filed on Jun. 12, 2006, now U.S. Pat. No. Re. 42,194; which also claims benefit under 35 U.S.C. §120 as a continuation of U.S. patent application Ser. No. 10/423,332 filed on Apr. 24, 2003, now U.S. Pat. No. Re. 39,133; which is also a reissue of U.S. Pat. No. 6,226,548 issued on May 1, 2001; which claims rights under 35 U.S.C. §119 of provisional application No. 60/059,915, filed on Sep. 24, 1997.*

*U.S. patent application Ser. No. 13/036,939, filed on Feb. 28, 2011, now U.S. Pat. No. Re. 44,305, issued on Jun. 18, 2013; also claims benefit under 35 U.S.C. §120 as a continuation of U.S. patent application Ser. No. 11/451,595, filed on Jun. 12, 2006, now U.S. Pat. No. Re. 42,226; which also claims benefit under 35 U.S.C. §120 as a continuation of U.S. patent application Ser. No. 10/423,332 filed on Apr. 24, 2003; which is a reissue of U.S. Pat. No. 6,226,548 issued on May 1, 2001; which claims rights under 35 U.S.C. §119 of provisional application No. 60/059,915, filed on Sep. 24, 1997.*

The present invention claims rights under 35 U.S.C. §119 on provisional application No. 60/059,915, filed on Sep. 24, 1997, and entitled "Percutaneous Registration Apparatus and Method for Use in Computer-Assisted Surgical Navigation."

FIELD OF THE INVENTION

The present invention relates generally to guiding, directing, or navigating instruments or implants in a body percutaneously, in conjunction with systems that use and generate images during medical and surgical procedures, which images assist in executing the procedures and indicate the relative position of various body parts, surgical implants, and instruments. In particular the invention relates to apparatus and minimally invasive procedures for navigating instruments and providing surgical implants percutaneously in the spine, for example, to stabilize the spine, correct deformity, or enhance fusion in conjunction with a surgical navigation system for generating images during medical and surgical procedures.

BACKGROUND OF THE INVENTION

Typically, spinal surgical procedures used, for example, to provide stabilization, fusion, or to correct deformities, require large incisions and substantial exposure of the spinal areas to permit the placement of surgical implants such as, for example, various forms of screws or hooks linked by rods, wires, or plates into portions of the spine. This standard procedure is invasive and can result in trauma, blood loss, and post operative pain. Alternatively, fluoroscopes have been used to assist in placing screws beneath the skin. In this alternative procedure at least four incisions must be made in the patient's back for inserting rods or wires through previously inserted screws. However, this technique can be difficult in that fluoroscopes only provide two-dimensional images and require the surgeon to rotate the fluoroscope frequently in order to get a mental image of the anatomy in three dimensions. Fluoroscopes also generate radiation to which the patient and surgical staff may become over exposed over time. Additionally, the subcutaneous implants required for this procedure may irritate the patient. A lever arm effect can also occur with the screws that are not connected by the rods or wires at the spine. Fluoroscopic screw placement techniques have traditionally used rods or plates that are subcutaneous to connect screws from vertebra to vertebra. This is due in part to the fact that there is no fluoroscopic technique that has been designed which can always adequately place rods or plates at the submuscular region (or adjacent to the vertebrae). These subcutaneous rods or plates may not be well tolerated by the patient. They also may not provide the optimal mechanical support to the spine because the moment arm of the construct can be increased, thereby translating higher loads and stresses through the construct.

A number of different types of surgical navigation systems have been described that include indications of the positions of medical instruments and patient anatomy used in medical or surgical procedures. For example, U.S. Pat. No. 5,383,454 to Bucholz; PCT Application No. PCT/US94/04530 (Publication No. WO 94/24933) to Bucholz; and PCT Application No. PCT/US95/12894 (Publication No. WO 96/11624) to Bucholz et al., the entire disclosures of which are incorporated herein by reference, disclose systems for use during a medical or surgical procedure using scans generated by a scanner prior to the procedure. Surgical navigation systems typically include tracking means such as, for example, an LED array on the body part, LED emitters on the medical instruments, a digitizer to track the positions of the body part and the instruments, and a display for the position of an instrument used in a medical procedure relative to an image of a body part.

Bucholz et al. WO 96/11624 is of particular interest, in that it identifies special issues associated with surgical navigation in the spine, where there are multiple vertebral bodies that can move with respect to each other. Bucholz et al. describes a procedure for operating on the spine during an open process where, after imaging, the spinous process reference points may move with respect to each other. It also discloses a procedure for modifying and repositioning the image data set to match the actual position of the anatomical elements. When there is an opportunity for anatomical movement, such movement degrades the fidelity of the pre-procedural images in depicting the intra-procedural anatomy. Therefore, additional innovations are desirable to bring image guidance to the parts of the body experiencing anatomical movement.

Furthermore, spinal surgical procedures are typically highly invasive. There is, thus, a need for more minimally invasive techniques for performing these spinal procedures, such as biopsy, spinal fixation, endoscopy, spinal implant insertion, fusion, and insertion of drug delivery systems, by reducing incision size and amount. One such way is to use surgical navigation equipment to perform procedures percutaneously, that is beneath the skin. To do so by means of surgical navigation also requires apparatus that can indicate the position of the spinal elements, such as, for example the vertebrae, involved in the procedure relative to the instruments and implants being inserted beneath the patient's skin and into the patient's spine. Additionally, because the spinal elements naturally move relative to each other, the user requires the ability to reorient these spinal elements to align with earlier scanned images stored in the surgical navigation system computer, to assure the correct location of those elements relative to the instruments and implants being applied or inserted percutaneously.

In light of the foregoing, there is a need in the art for apparatus and minimally invasive procedures for percutaneous placement of surgical implants and instruments in the spine, reducing the size and amount of incisions and utilizing surgical navigation techniques.

SUMMARY OF THE INVENTION

Accordingly, the present invention is directed to apparatus and procedures for percutaneous placement of surgical implants and instruments such as, for example, screws, rods, wires and plates into various body parts using image guided surgery. More specifically, one object of the present invention is directed to apparatus and procedures for the percutaneous placement of surgical implants and instruments into various elements of the spine using image guided surgery.

To achieve these objects and other advantages and in accordance with the purpose of the invention, as embodied and broadly described herein, the invention includes an apparatus for use with a surgical navigation system and comprises an attaching device rigidly connected to a body part, such as the spinous process of a vertebrae, with an identification superstructure rigidly but removably connected to the attaching device. This identification superstructure is a reference arc and fiducial array, which accomplishes the function of identifying the location of the superstructure, and, therefore, the body part to which it is fixed, during imaging by CAT scan or MRI, and later during medical procedures.

In one aspect, the attaching device is a clamp with jaws and sharp teeth for biting into the spinous process.

In another aspect, the fixture is a screw, having a head, wherein the screw is implanted into the spinous process and a relatively rigid wire is attached to the head of the screw and also implanted into the spinous process at an angle to the axis of the screw to prevent the screw from rotating in either direction.

In another aspect, the superstructure includes a central post, and a fiducial array and a reference arc rigidly but removably attached to the central post. The fiducial array is composed of image-compatible materials, and includes fiducials for providing a reference point, indicating the position of the array, which are rigidly attached to the fiducial array, composed of, for example titanium or aluminum spheres. The reference arc includes emitters, such as, for example Light Emitting Diodes ("LEDs"), passive reflective spheres, or other tracking means such as acoustic, magnetic, electromagnetic, radiologic, or micropulsed radar, for indicating the location of the reference arc and, thus, the body part it is attached to, during medical procedures.

In addition, the invention further comprises a method for monitoring the location of an instrument, surgical implants and the various portions of the body, for example, vertebrae, to be operated on in a surgical navigation system comprising the steps of: attaching a fixture to the spinous process; attaching a superstructure including a fiducial array with fiducials and a reference arc to the fixture; scanning the patient using CT, MRI or some other three-dimensional method, with fiducial array rigidly fixed to patient to identify it on the scanned image; and thereafter, in an operating room, using image-guided technology, touching an image-guided surgical pointer or other instrument to one or more of the fiducials on the fiducial array to register the location of the spinal element fixed to the array and emitting an audio, visual, radiologic, magnetic or other detectable signal from the reference arc to an instrument such as, for example, a digitizer or other position-sensing unit, to indicate changes in position of the spinal element during a surgical procedure, and performing a surgical or medical procedure percutaneously on the patient using instruments and implants locatable relative to spinal elements in a known position in the surgical navigation system.

In another aspect, the method includes inserting screws or rigid wires in spinal elements in the area involved in the anticipated surgical procedure before scanning the patient, and after scanning the patient and bringing the patient to the operating area, touching an image-guided or tracked surgical pointer to these screws and wires attached to the vertebrae to positively register their location in the surgical navigation computer, and manipulating either the patient's spine or the image to align the actual position of the spinal elements with the scanned image.

In another aspect, the method includes percutaneously implanting screws into spinal elements, which screws are located using image guided surgical navigation techniques, and further manipulating the orientation of the screw heads percutaneously using a head-positioning probe containing an emitter, that can communicate to the surgical navigation computer the orientation of the screw heads and position them, by use of a specially designed head-positioning tool with an end portion that mates with the heads of the screws and can rotate those screw heads to receive a rod, wire, plate, or other connecting implant. If a rod is being inserted into the screw heads for example, the method further includes tracking the location and position of the rod, percutaneously using a rod inserter having one or more emitters communicating the location and orientation of the rod to the surgical navigation computer.

The objects of the invention are to provide a user, such as a surgeon, with the system and method to track an instrument and surgical implants used in conjunction with a surgical navigation system in such a manner to operate percutaneously on a patient's body parts, such as spinal vertebrae which can move relative to each other.

It is a further object of this invention to provide a system and method to simply and yet positively indicate to the user a change in position of body parts, such as spinal vertebrae segments, from that identified in a stored image scan, such as from an MRI or CAT scan, and provide a method to realign those body parts to correspond with a previously stored image or the image to correspond with the actual current position of the body parts.

It is a further object of this invention to provide a system or method for allowing a fiducial array or reference arc that is removable from a location rigidly fixed to a body part and replaceable back in that precise location.

It is another object of this invention to provide a system and method for positively generating a display of instruments and surgical implants, such as, for example screws and rods, placed percutaneously in a patient using image-guided surgical methods and techniques.

It is another object of this invention for a percutaneous reference array and fiducial array, as described in this appplication, to be used to register and track the position of the vertebrae for the purposes of targeting a radiation dose to a diseased portion of said vertebrae using a traditional radiosurgical technique.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in this description.

It is to be understood that both the foregoing general description and the following detailed description are exemplary and explanatory only and are not restrictive of the invention.

BRIEF DESCRIPTION OF THE DRAWINGS

The accompanying drawings, which are incorporated in and constitute a part of this specification, illustrate one embodiment of the invention and together with the description, serve to explain the principles of the invention.

DETAILED DESCRIPTION OF THE PREFERRED EMBODIMENT

Reference will now be made in detail to the present preferred embodiment of the invention, an example of which is illustrated in the accompanying drawings. Wherever possible, the same reference numbers will be used throughout the drawings to refer to the same or like parts. The following example is intended to be purely exemplary of the invention.

Figure 1:
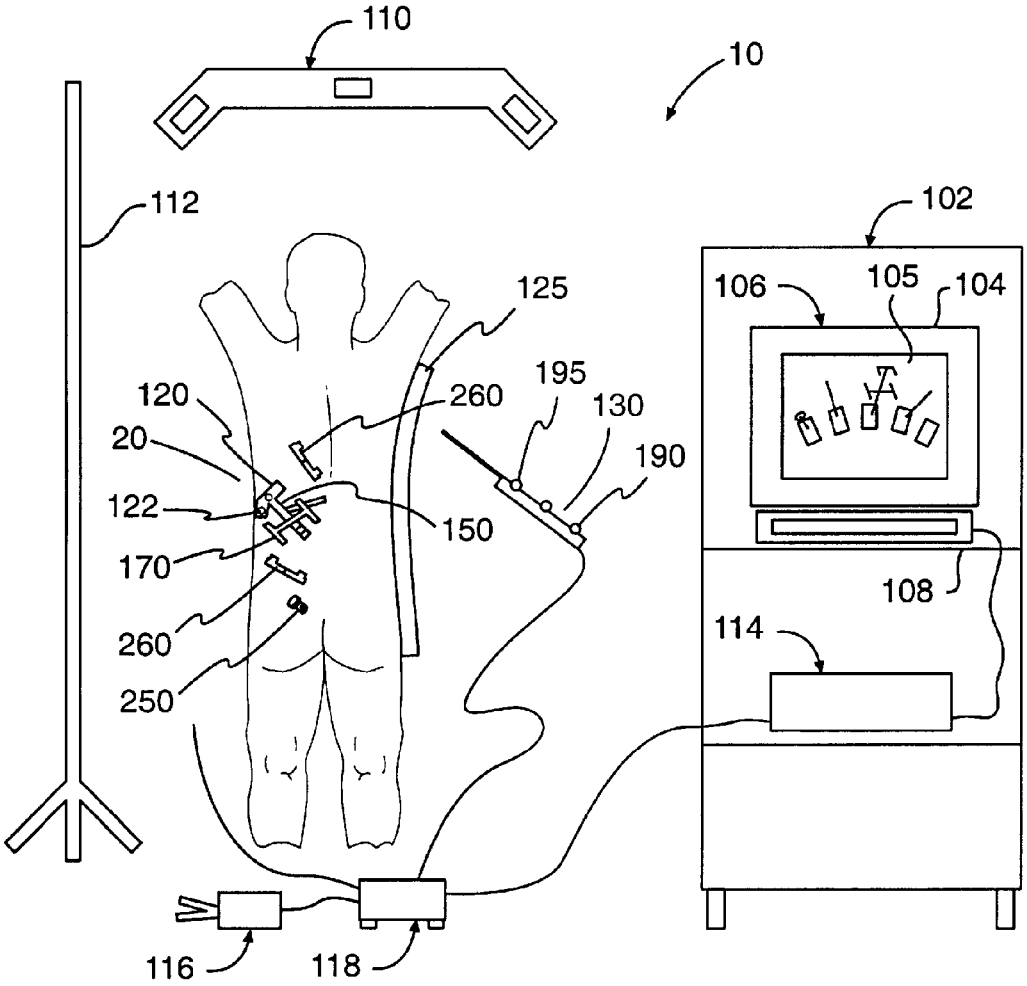
FIG. 1 is a schematic diagram of one preferred embodiment of a superstructure for use in the current invention, including a reference arc, center post and fiducial array and rigid Kirschner wires ("K wires") and screws placed in the spine for use with a surgical navigation system for percutaneous spinal surgical procedures.

As generally described in PCT/US95/12894, the entire disclosure of which is incorporated herein by reference, a typical surgical navigation system is shown in FIG. 1 adopted to be used in the present invention. A computer assisted image-guided surgery system, indicated generally at 10, generates an image for display on a monitor 106 representing the position of one or more body elements, such as spinal elements fixedly held in a stabilizing frame or device such as a spinal surgery frame 125 commonly used for spinal surgery. A reference arc 120 bearing tracking means or emitters, such as for example LED emitters 122, is mounted to the spinous process by a central post 150. The structures 20 and K wires 260 of FIG. 1 are depicted in more detail in FIG. 1A. The image 105 is generated from an image data set, usually generated preoperatively by a CAT scanner or by MRI for example, which image 105 has reference points for at least one body element, such as a spinal element or vertebrae. The reference points of the particular body element have a fixed spatial relation to the particular body element.

The system includes an apparatus such as a digitizer or other Position Sensing Unit (PSU), such as for example sensor array 110 on support 112 for identifying, during the procedure, the relative position of each of the reference points to be displayed by tracking the position of emitters 122 on arc 120. The system also includes a processor 114 such as a PC or other suitable workstation processor associated with controller 108 for modifying the image data set according to the identified relative position of each of the reference points during the procedure, as identified by digitizer 110. The processor 114 can then, for example, generate an image data set representing the position of the body elements during the procedure for display on monitor 106. A surgical instrument 130, such as a probe or drill or other tool, may be included in the system, which is positioned relative to a body part and similarly tracked by sensor array 110.

In summary, the general operation of a surgical navigating system is well known in the art and need not further be described here.

Figure 2:
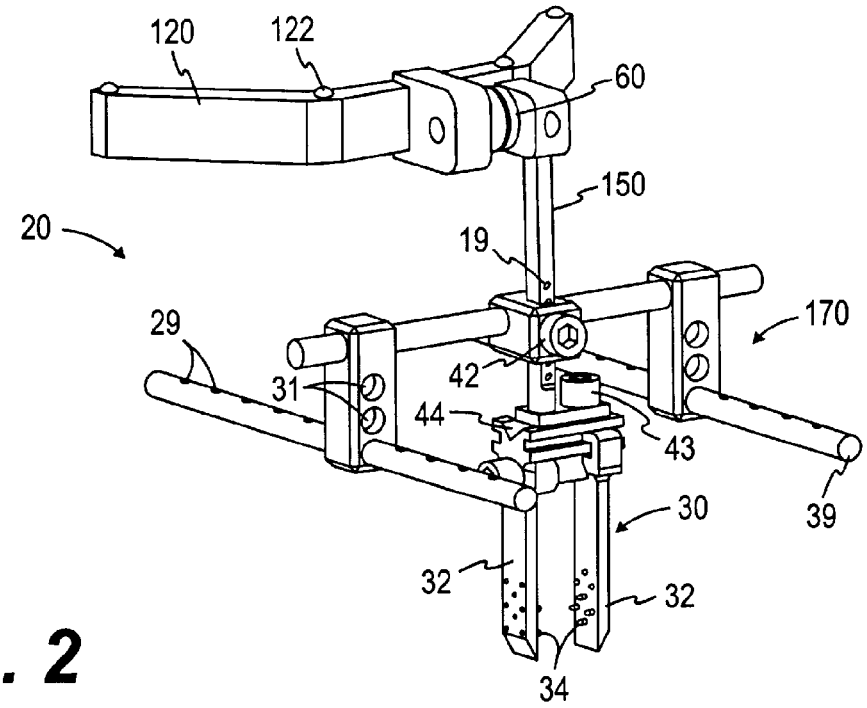
FIG. 2 is a diagram of the preferred embodiment of a clamp fixture for rigid connection to the spinous process of a single vertebrae with an H-shaped fiducial array attached to a center post rigidly attached to the clamp and a mating connector at the tip of the post for mating with a reference array, and a reference array for use in the current invention.
Figure 2A:
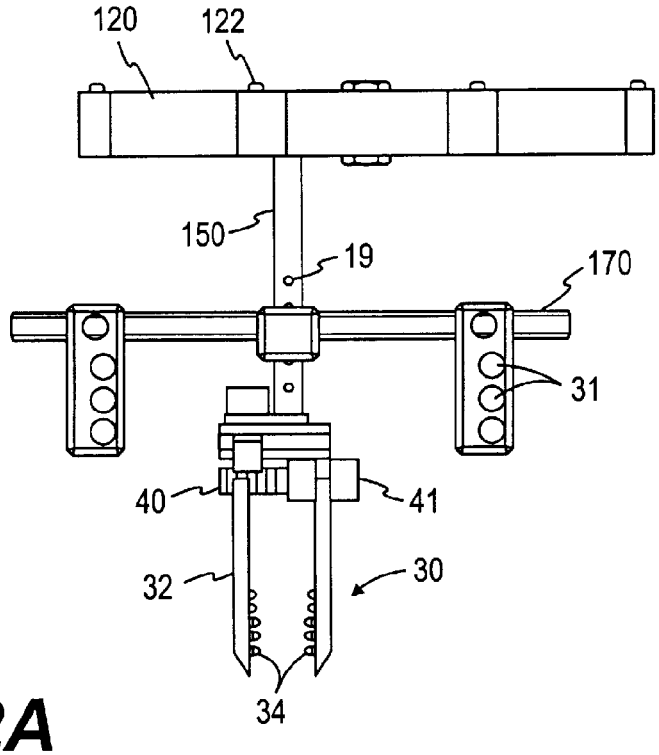
FIG. 2A is a side view of FIG. 2
Figure 2B:
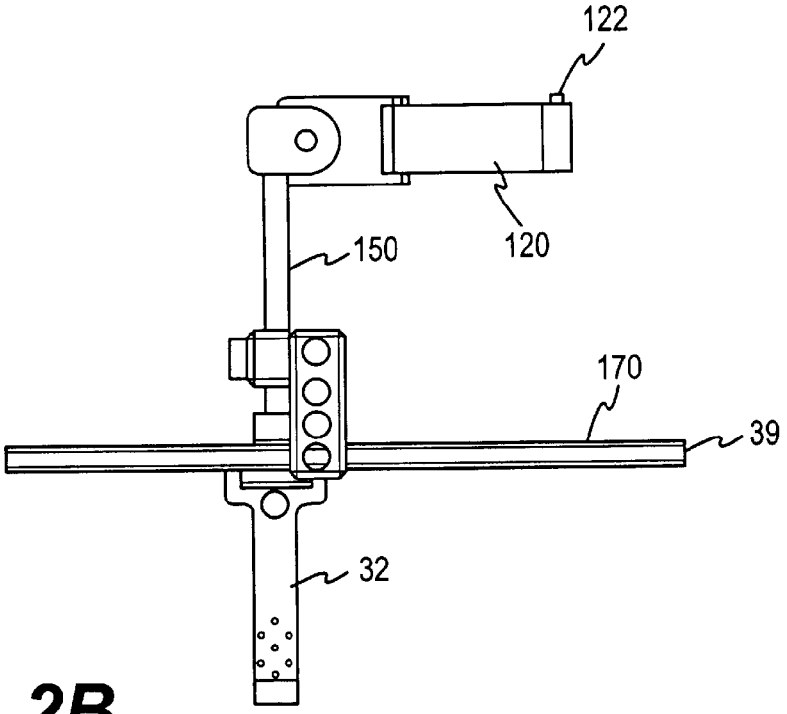
FIG. 2B is another side view of FIG. 2.
Figure 2C:
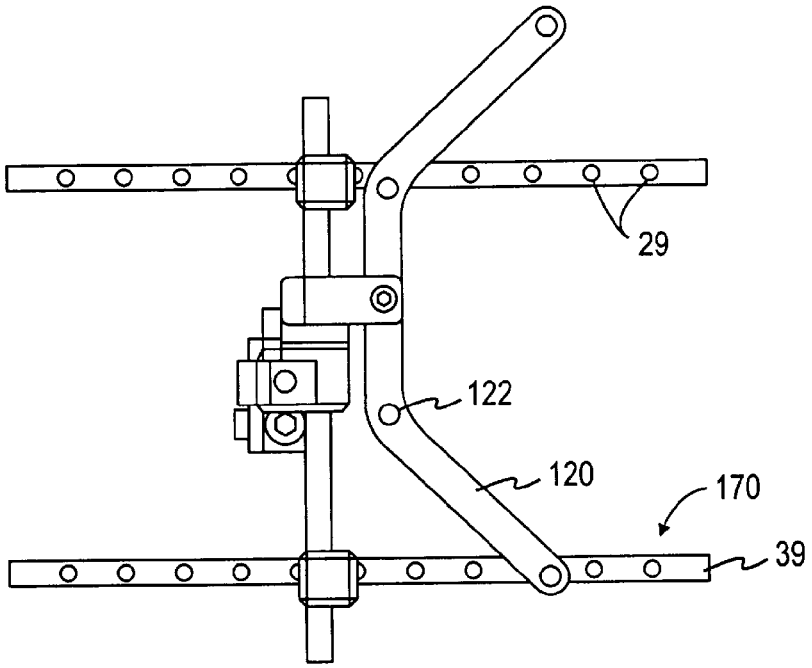
FIG. 2C is a top view of FIG. 2.

In accordance with the preferred embodiment of the present invention, with further reference to FIGS. 1 through 6, a registration device 20 is rigidly fixed to a spinal element by, for example, a device such as a bone clamp 30 depicted in FIG. 2. Alternatively, a screw retention device 40, such as the cannulated screw 42 depicted in FIG. 5, and described in more detail below, can be used.

Figure 1A:
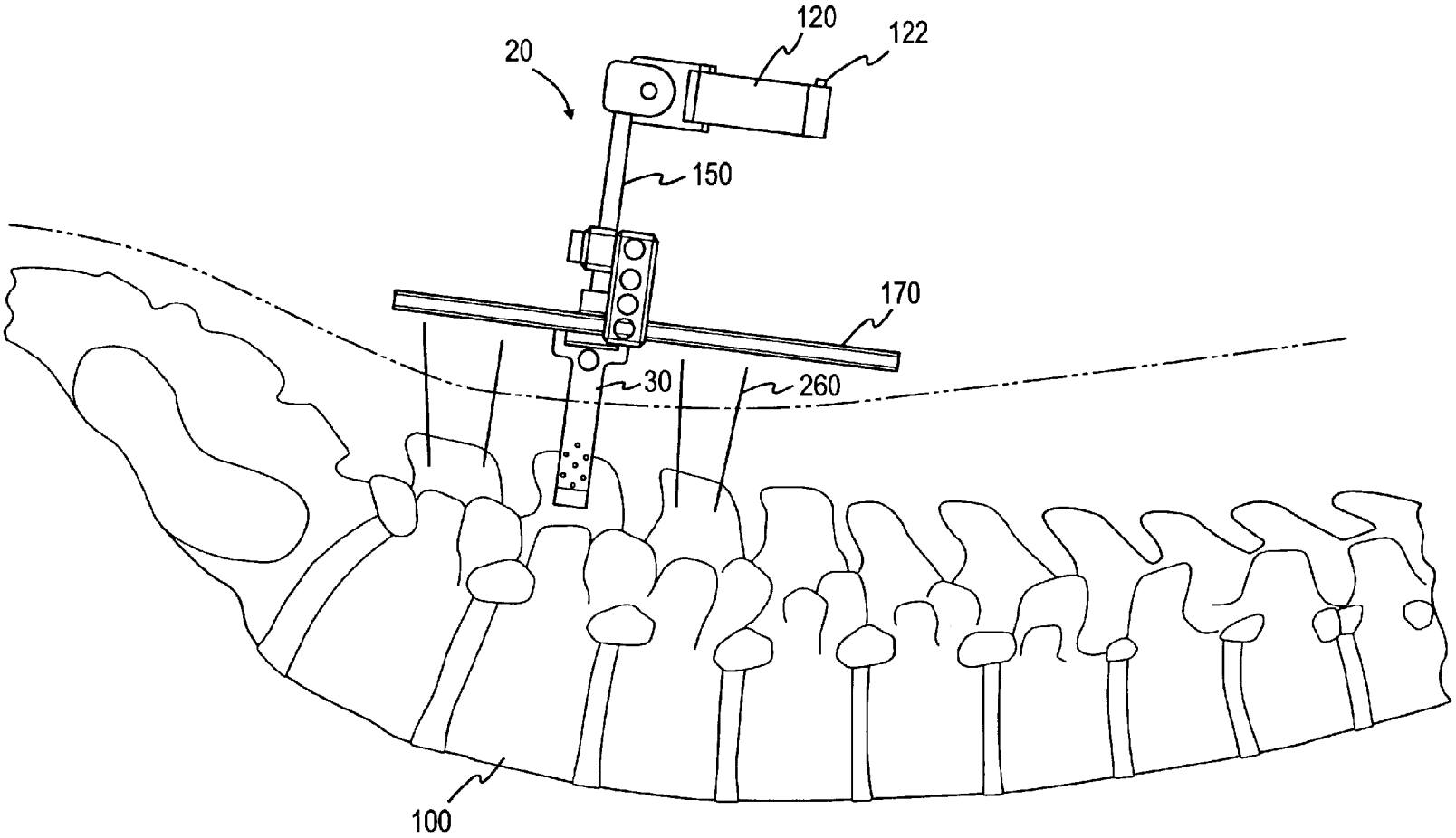
FIG. 1A is an enlarged view of the superstructure depicted in FIG. 1 engaging a vertebra by a clamp and also K wires implanted in adjacent vertebrae in the superior and inferior positions of the spinous process.
Figure 2D:
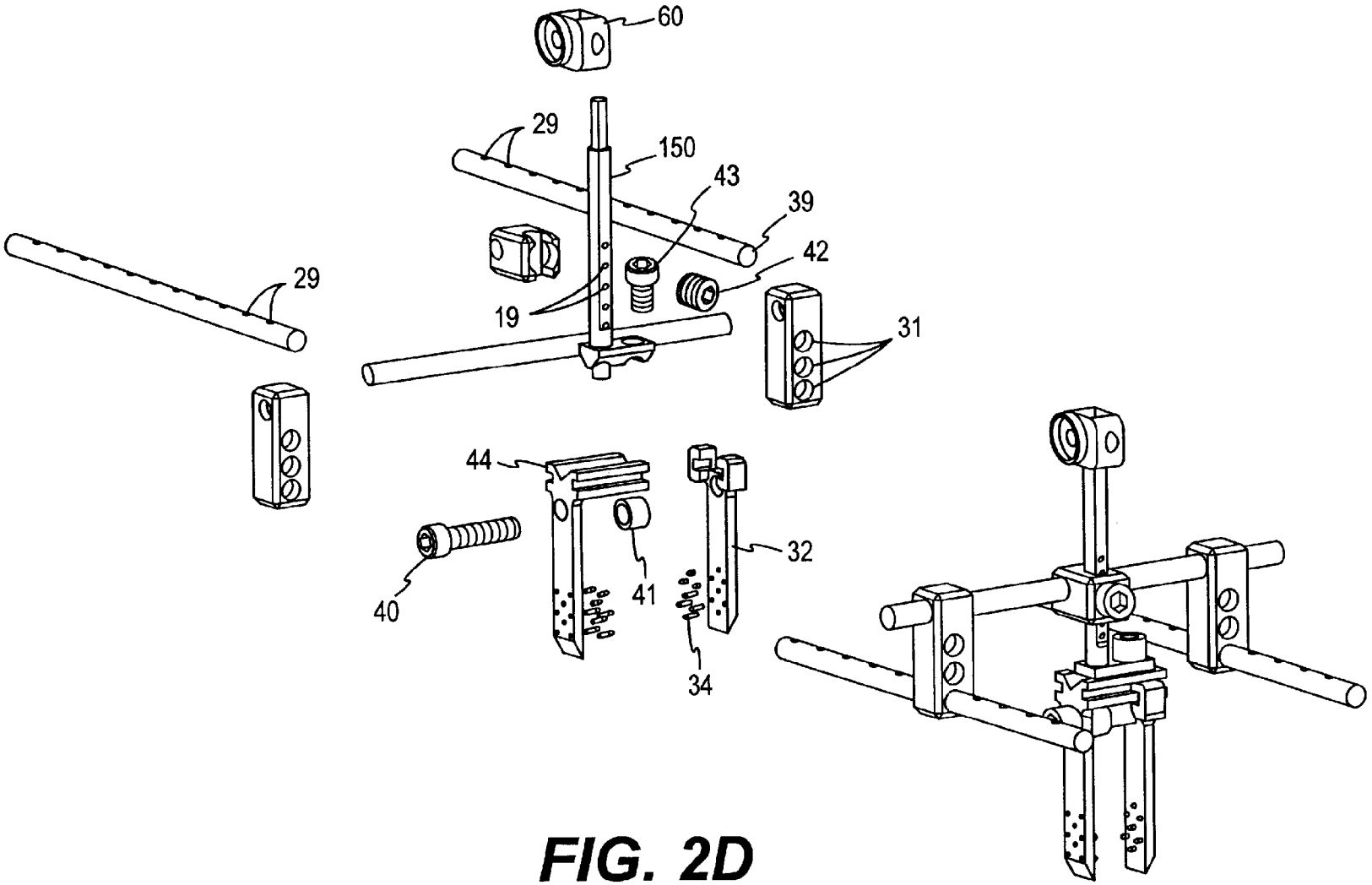
FIG. 2D is an exploded view of FIG. 2 without the reference arc.
Figure 2E:
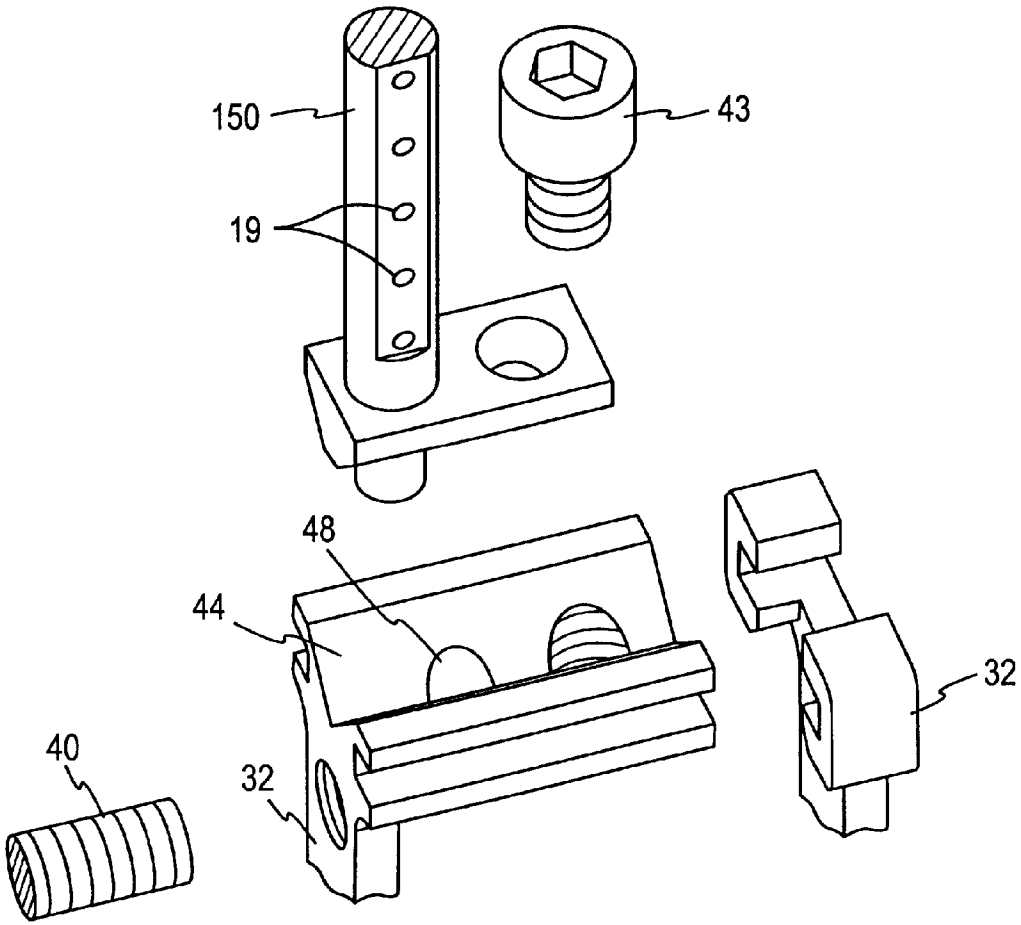
FIG. 2E is an exploded view of the interface of the center post and clamp of FIG. 2.
Figure 11:
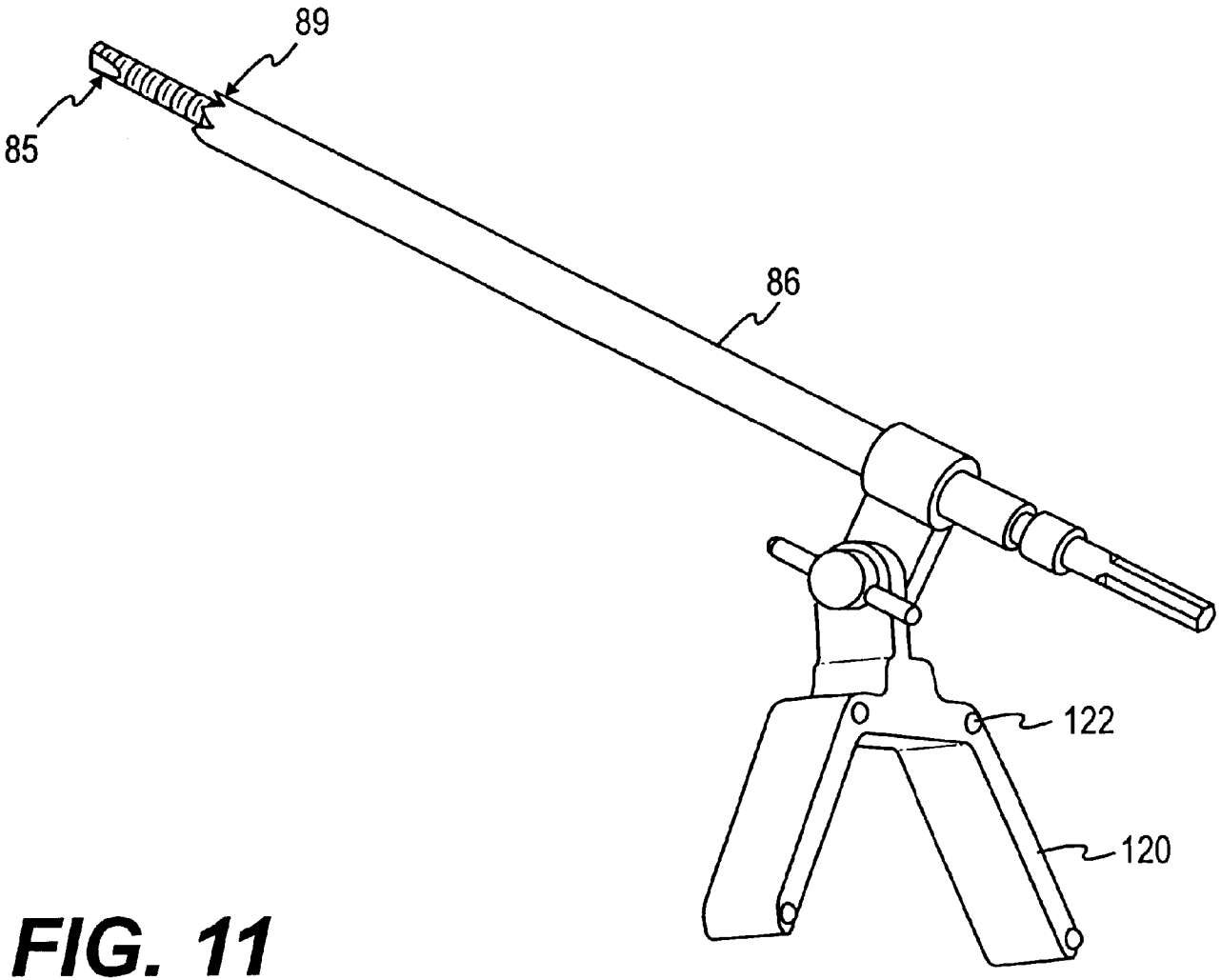
FIG. 11 is a diagram of the cannulated tube of FIG. 10 with a reference arc and screw for attachment to a spinal process.

With reference now to FIG. 2, bone clamp 30 is fixedly attached to the spinous process. The clamp 30 includes at so least two blades (or jaws) 32 with tips or teeth 34, which are preferably sharp, for driving together and penetrating soft tissue or more dense bone for rigid fixation to the spinous process. The teeth 34 are also preferably sized to accommodate the bulb shape of the spinous process. The driving mechanism 40 is, for example, a screw driven into a sleeve 41 and is also preferably located such that it will be accessible in a percutaneous manner. Attached to the clamp 30 is a superstructure 20. The superstructure 20 includes a central post 150 which is relocatable, that is, it fixes to the clamp 30 in a rigid fashion, for example, as depicted in FIGS. 2D and 2E, by being inserted into a V-shaped wedge 44 orienting the post 150 front to back and providing a mating hole 48 along the wedge 44 for insertion of post 150 in a single orientation and also providing fasteners such as screw 43 for tightning to lock the post 150 in place. The post 150 can be removed and reapplied by loosening and tightening screw 43, such that the original geometry and orientation is maintained. The central post 150 has at its apex a connector 60 with unique geometrical configuration, such as, for example, a starburst, onto which a spinal reference arc 120 of the superstructure 20 attaches. Any such standard reference arc 120 can be used, such as depicted in FIGS. 1A, 4, and 11, preferably including emitters 122, such as for example LEDs or reflective spheres for providing a positive indication of movement to the surgical navigation system during a procedure.

Figure 3:
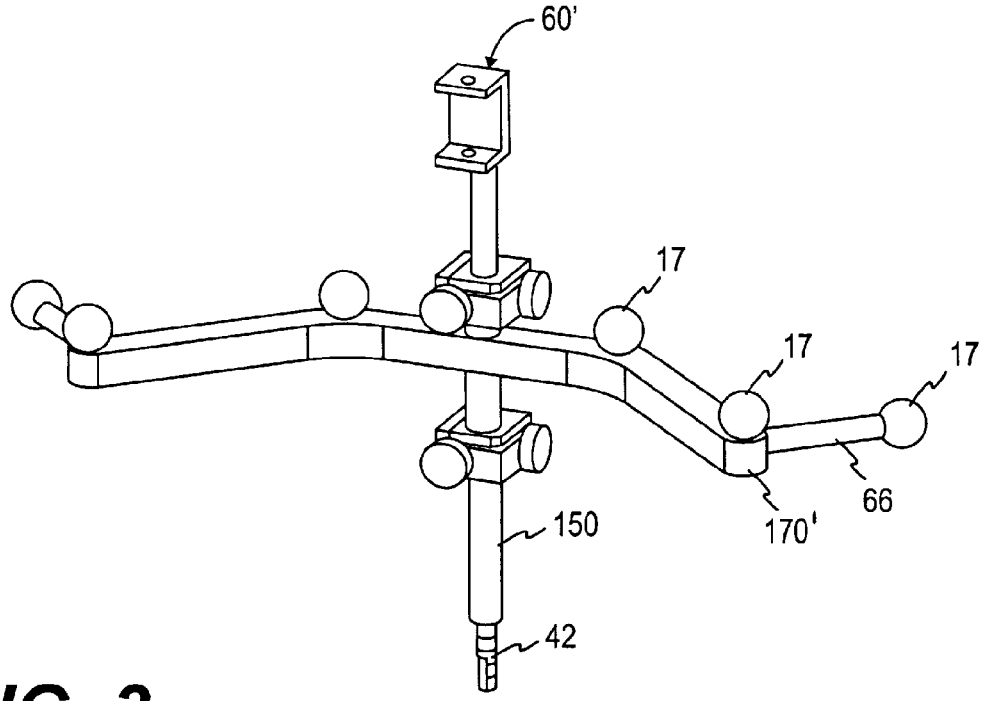
FIG. 3 is a diagram of a W-Shaped fiducial array mounted to a central post with generally spherical fiducials attached to the array, for mounting to a single vertebrae.
Figure 3A:
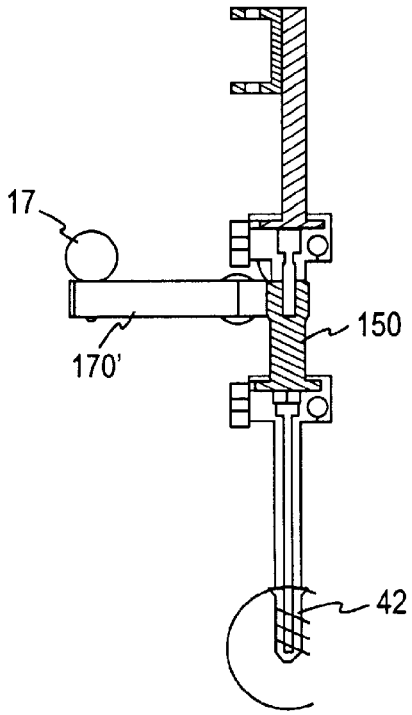
FIG. 3A is a side view of FIG. 3.
Figure 3B:
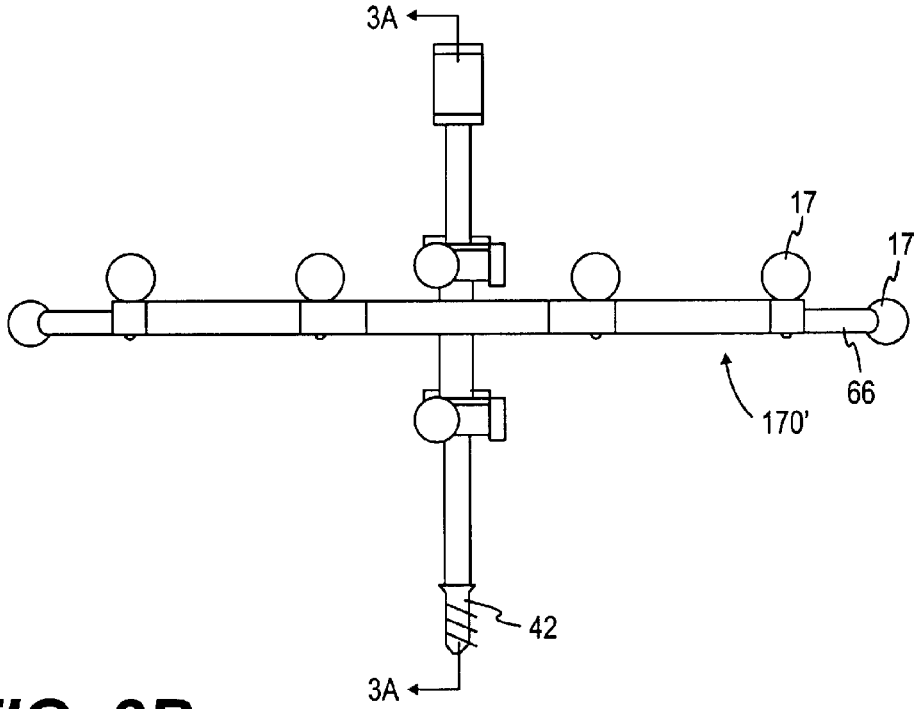
FIG. 3B is another side view of FIG. 3.
Figure 3C:
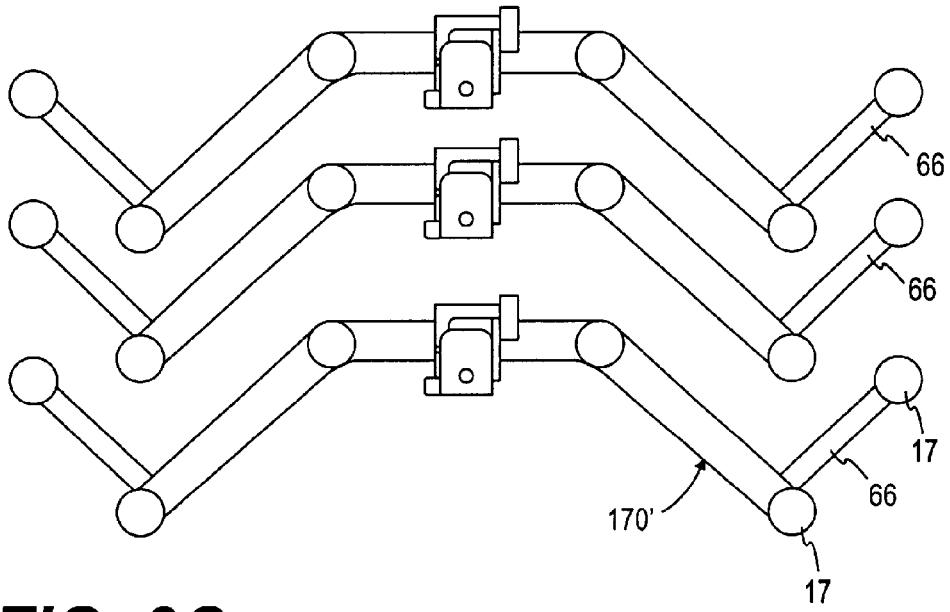
FIG. 3C is a top view of FIG. 3.
Figure 4:
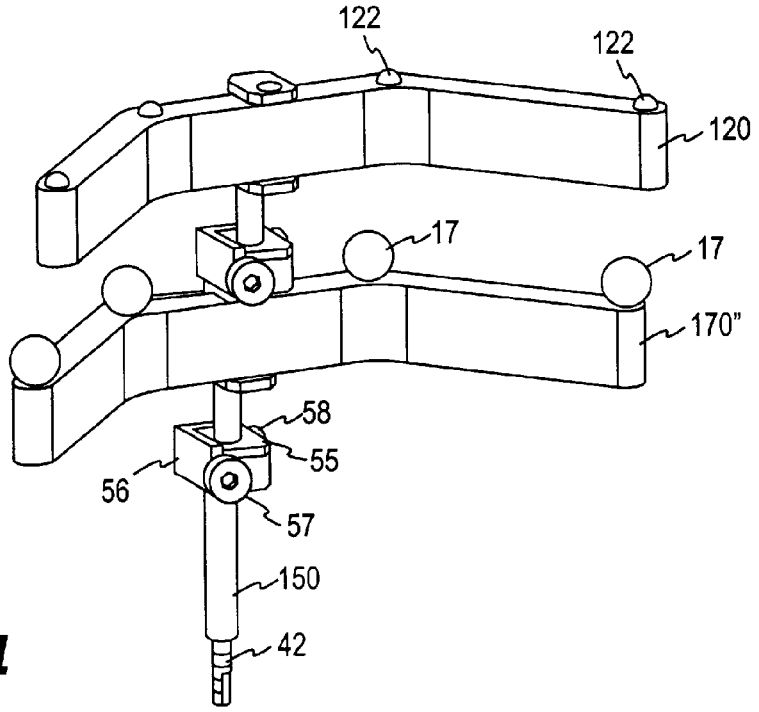
FIG. 4 is a diagram of a reference arc and fiducial attached to a center post for use in the current invention in mounting to a single vertebrae.
Figure 4A:
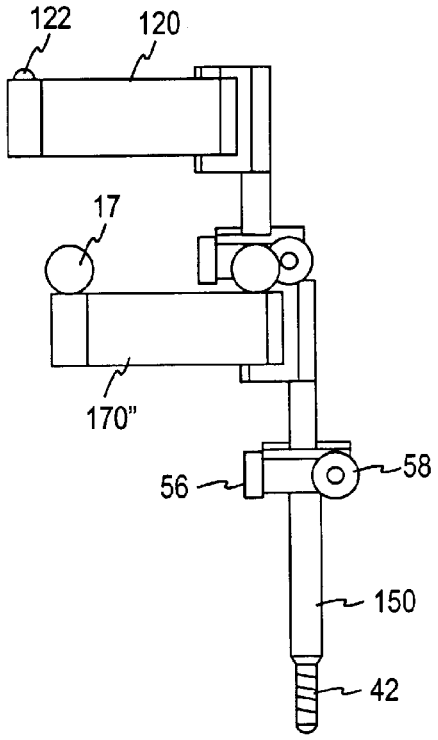
FIG. 4A is a side view of FIG. 4.
Figure 4B:
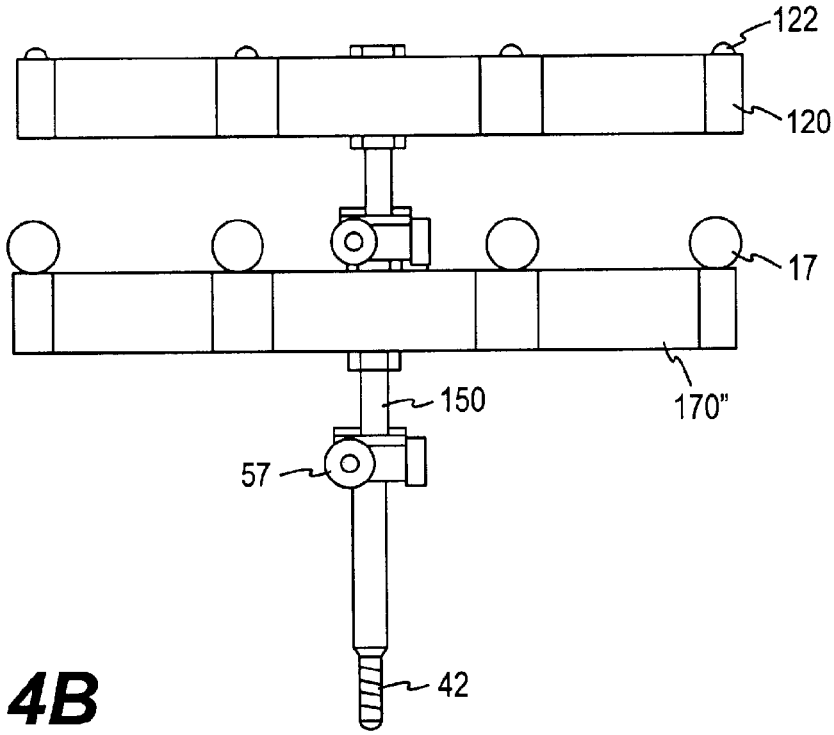
FIG. 4B is a back view of FIG. 4.
Figure 4C:
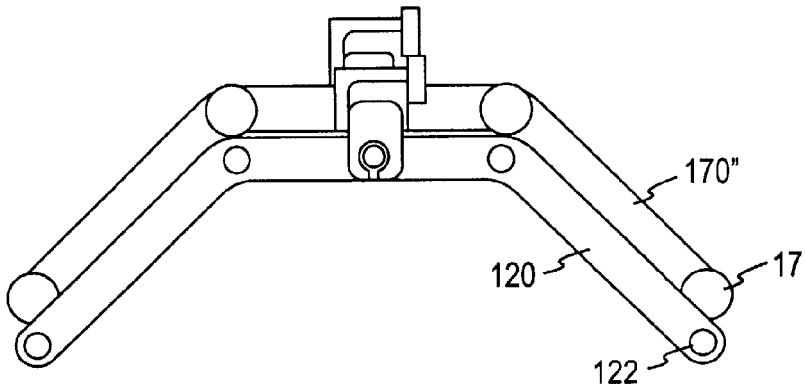
FIG. 4C is a top view of FIG. 4.
Figure 5:
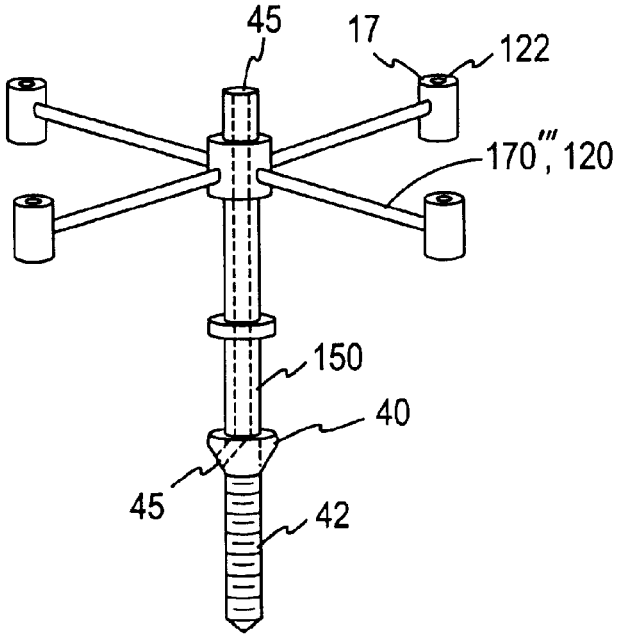
FIG. 5 is a diagram of an alternative embodiment of a fixture for use in the current invention using a cannulated screw for insertion into a vertebrae, with Kirschner wire mounted on a central post and including an alternate embodiment of a fiduciary array and reference arc combined on a single structure.

Also rigidly attached to the central post 150, as part of the superstructure 20 preferably at a location closer to the skin, or possibly collocated with or also performing the function of the reference arc 120, is a fiducial array 170, which can be of various different shapes, such as, for example the H-shaped frame 170 depicted in FIG. 2, the W-shaped frame 170' as depicted in FIG. 3, the U-shaped frame 170" as depicted in FIG. 4 or the X-shaped frame 120', 170'" depicted in FIG. 5 (depicting a structure that is both a fiducial array and a reference arc). As depicted in FIGS. 2 and 3, this array can include fiducial points 29 or spheres 17, rigidly attached to fiducial array 170, 170' and is, for example, as depicted in FIG. 3, substantially in the shape of spheres 17 and of a material detectable by the CAT scan or MRI, preferably titanium or aluminum. This fiducial array such as 170 indicates to the surgical navigation system the location of the bone structure to which the clamp 30 and central post 150 are attached by touching a pointed surgical tracker to fiducial points 29 or a cup-shaped probe to fiducial spheres 17, thereby indicating the center of the fiducial to the surgical navigation controller 114. The array 170 and central post 150 are also attached to the clamp 30, as described above, in such a way that they can be removed and replaced in the same geometric orientation and location, for example, by means of a uniquely shaped interface, for example, a triangle, or a single unique shape or a combination of unique angles or pins with the clamp 30 such that the post 150 can only be reinserted the same way it was removed.

Additionally, the fiducial array 170, can be located at various heights on the post 150 to accomodate variations in patient tissue depth and size, preferably as close to the patient's body as possible, and then fixed at that specific height by the use of pins or indents matched to holes 19 (shown in FIG. 2) in the central post 150 or by placing the rods 39 of H-shaped array 170 in different holes 31. The fiducial array 170 also has, for example, divots 29 (shown in FIG. 2) shaped to interface with an instrument such as a surgical pointer 130 which can touch that divot 29 to register the location of the divot 29 and, thus, the location of the fiducial array 170 and likewise the spinal element in the surgical navigation system. Multiple divots can be registered to further increase accuracy of the registration system. In one preferred embodiment of the array, the fiducials 17 or 29 can be mounted in a manner such that they can be adjusted, for example by mounting them on a rotatable or collapsible arm 66 (as depicted in FIG. 3) that pivots and folds together, to get the maximum distance between fiducials while not dramatically increasing the field of view required at the time of scanning.

Figure 6:
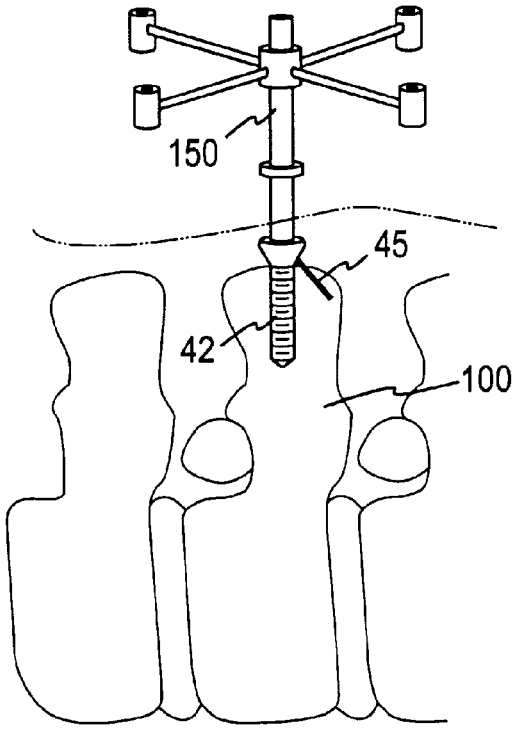
FIG. 6 is a side view of the screw and Kirschner wire fixture of FIG. 5 implanted in a spinous process of a vertebrae.

Alternatively, rather than using clamp 30, a screw 42 and rigid wire 45 attachment, as depicted in FIGS. 5 and 6, may be used to rigidly attach the central post of the superstructure 20 to a body element, such as, for example, a vertebrae. As depicted in FIG. 6, screw 42 is screwed into the spinal process of spinal element 100. A rigid wire 45, post, or other sufficiently rigid fastener such as for example a Kirschner wire (K-wire), is inserted through the cannulation in the center of post 150 and the screw 42 or is otherwise fixed to the screw 42, and exits the tip of the screw 42 at some angle, and is also implanted into the spinal element 100 to prevent the screw 42 from rotating in either direction.

Figure 10:
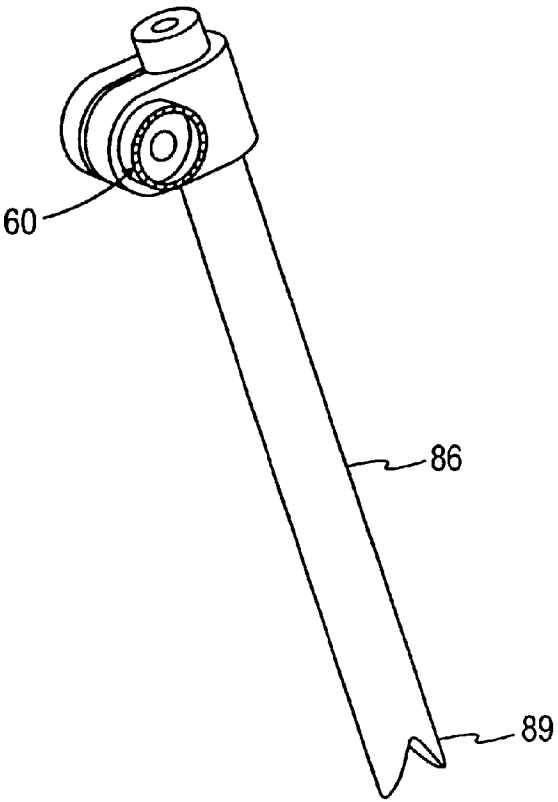
FIG. 10 is a diagram of an alternative embodiment of the invention depicting a cannulated tube and attachment for holding a reference arc.

Another embodiment for preventing the superstructure 20 from rotating as depicted in FIGS. 10 and 11 includes the insertion of a screw 85 through a cannulated tube 86 which has teeth 89 in the end (or V-shaped end) that would bite into the tip of the spinous process, preventing rotation.

Having described the preferred embodiment of this apparatus of the present system, the method of using this apparatus to practice the invention of registering a single vertebrae will now be discussed. The operation of a surgical navigating system is generally well known and is described in PCT/US95/12894. In the preferred method of operation, clamp 30 of FIG. 2 or screw 42 and K-Wire 45 of FIG. 5 are implanted percutaneously through a small incision in the skin and rigidly attached to the spinal process. This attachment occurs with the clamp 30, by driving the blades 32 of the clamp 30 together to hold the spinous process rigidly. The central post 150 is then rigidly fixed to the clamp 30 or screw 42 and the fiducial array 170 is rigidly fixed to the central post 150. The patient is then scanned and imaged with a CAT scan or MRI with a field of view sufficiently large to display the spinal anatomy and the clamp 30 or screw 42 and the fiducial array 170. This scan is loaded into the surgical navigation system processor 104.

Figure 4D:
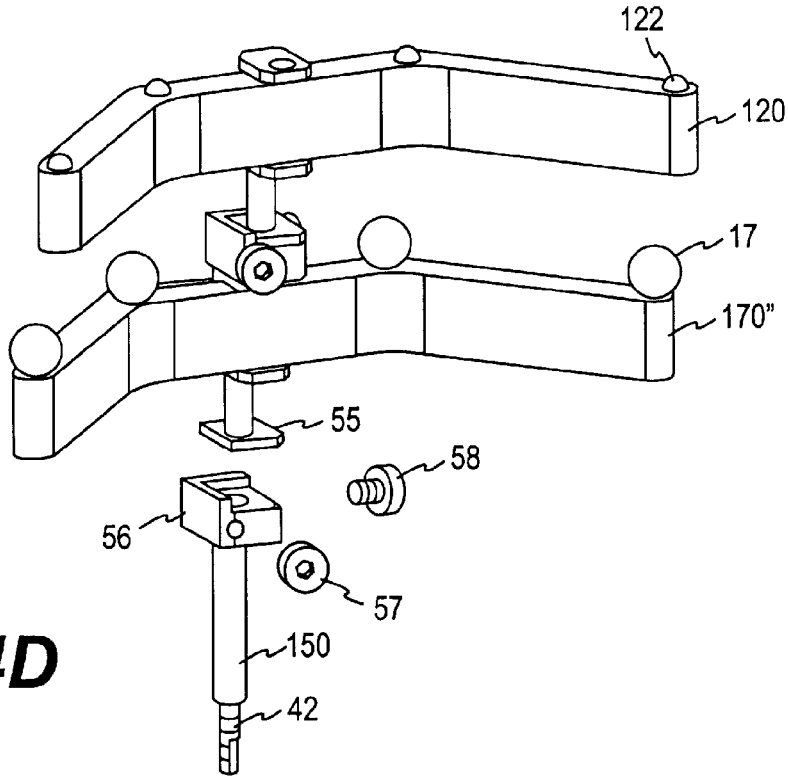
FIG. 4D is an expanded view of FIG. 4.
Figure 4E:
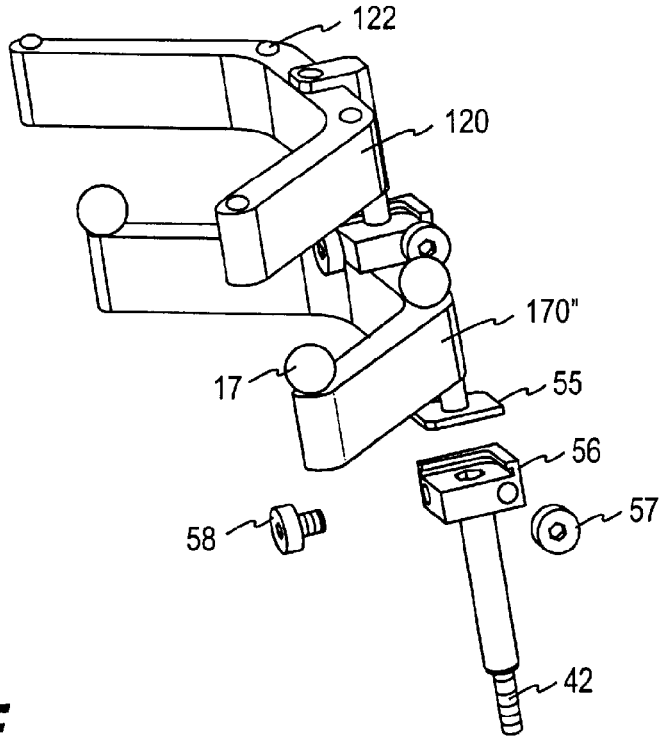
FIG. 4E is an expanded side view of FIG. 4.
Figure 4F:
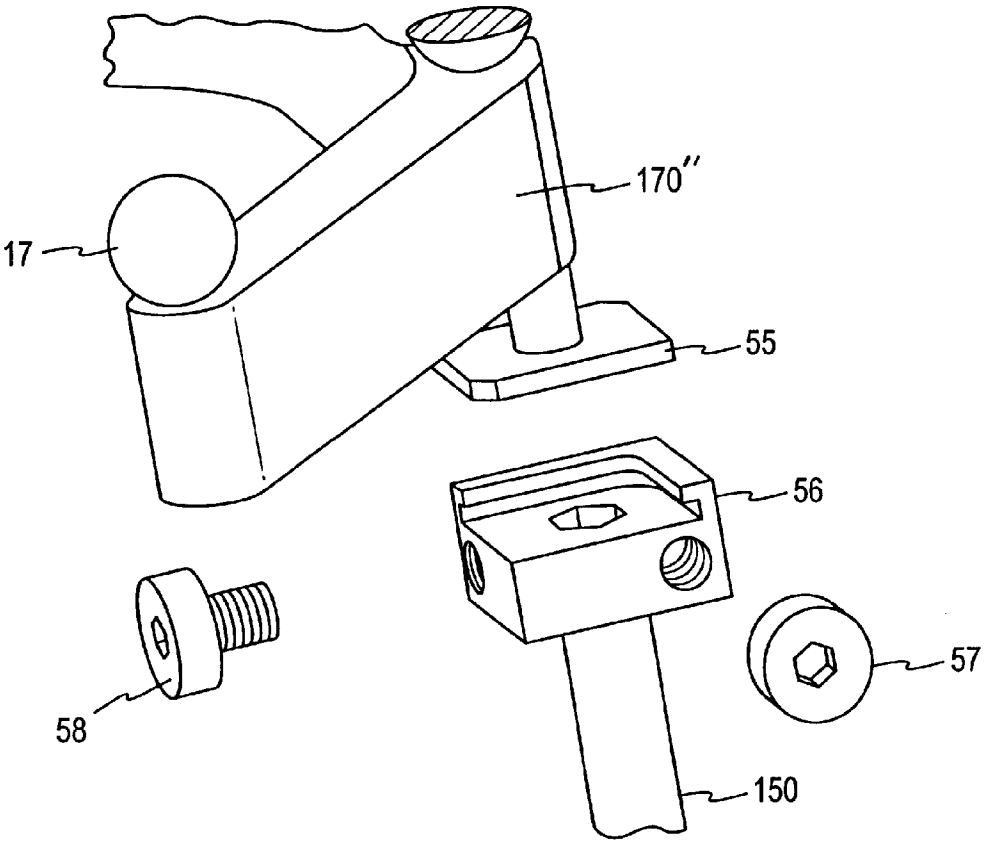
FIG. 4F is an expanded view of the array foot and shoe of FIG. 4E.

After scanning the patient, the array 120 and post 150 can be removed from the patient, while leaving in place the rigidly connected clamp 30 or screw 42. For example, as depicted in FIGS. 4D and 4E, a foot 55 located below array 170" engages with shoe 56 and rigidly connected by screws 57 and 58. Before the surgical procedure, the post 150, array 120 and other remaining portions of the superstructure 20, once removed, may be sterilized. The patient is then moved to the operating room or similar facility from, for example, the scanning room.

Once in the operating room, the patient may be positioned in an apparatus, such as, for example, a spinal surgery frame 125 to help keep the spinal elements in a particular position and relatively motionless. The superstructure 20 is then replaced on the clamp 30 or screw 42 in a precise manner to the same relative position to the spinal elements as it was in the earlier CAT scan or MRI imaging. The reference arc 120 is fixed to the starburst or other interface connector 60 on the central post 150 which is fixed to the clamp 30 or screw 42. The operator, for example a surgeon, then touches an instrument with a tracking emitter such as a surgical pointer 130 with emitters 195 to the divots 29 on the fiducial array 170 to register the location of the array 170 and, thus, because the spinal process is fixed to the fiducial array 170, the location of the spinal element is also registered in the surgical navigation system.

Once the superstructure 20 is placed back on the patient, any instrument 130 fitted with tracking emitters thereon such as, for example, a drill or screw driver, can be tracked in space relative to the spine in the surgical navigation system without further surgical exposure of the spine. The position of the instrument 130 is determined by the user stepping on a foot pedal 116 to begin tracking the emitter array 190. The emitters 195 generate infrared signals to be picked up by camera digitizer array 110 and triangulated to determine the position of the instrument 130. Additionally, other methods may be employed to track reference arcs, pointer probes, and other tracked instruments, such as with reflective spheres, or sound or magnetic emitters, instead of LED's. For example, reflective spheres can reflect infrared light that is emitted from the camera array 110 back to the camera array 110. The relative position of the body part, such as the spinal process is determined in a similar manner, through the use of similar emitters 122 mounted on the reference frame 120 in mechanical communication with the spinal segment. As is well known in this art and described generally in PCT/US95/12894, based upon the relative position of the spinal segment and the instrument 130 (such as by touching a known reference point) the computer would illustrate a preoperative scan—such as the proper CAT scan slice—on the screen of monitor 106 which would indicate the position of the tool 130 and the spinal segment for the area of the spine involved in the medical procedure.

For better access by the operator of various areas near the central post 150, the fiducial array 170 can be removed from the central post 150, by, for example, loosening screw 42 and sliding the array 170 off post 150, leaving the reference arc 120 in place or replacing it after removal of array 170. By leaving the reference arc 120 in place, the registration of the location of the spinal process is maintained. Additionally, the central post 150, reference arc 120, and fiducial array 170 can be removed after the spinal element has been registered leaving only the clamp 30 or screw 42 in place. The entire surgical field can then be sterilized and a sterile post 150 and reference arc 170 fixed to the clamp 30 or screw 42 with the registration maintained.

This surgical navigation system, with spinal element registration maintained, can then be used, for example, to place necessary and desired screws, rods, hooks, plates, wires, and other surgical instruments and implants percutaneously, using image-guided technology. Once the location of the spinal element 100 involved in the procedure is registered, by the process described above, in relation to the image data set and image 105 projected on monitor 106, other instruments 130 and surgical implants can be placed under the patient's skin at locations indicated by the instrument 130 relative to the spinal element 100.

Additionally, the location of other spinal elements, relative to the spinal element 100 containing the fiducial array 170, can be registered in the surgical navigation system by, for example, inserting additional screws 250, rigid wires 260, or other rigid implants or imageable devices into the spinal segment.

Figure 7:
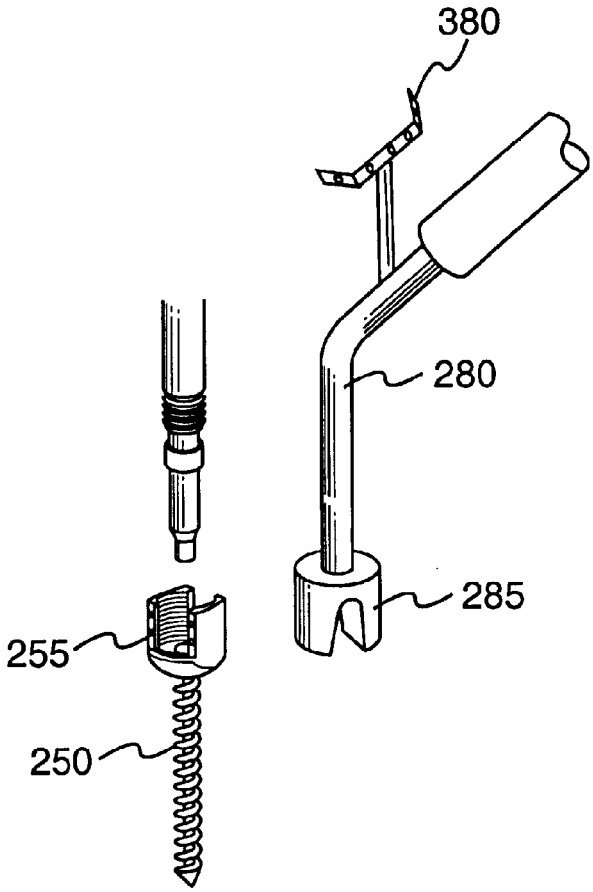
FIG. 7 is a diagram of a screw-head positioning probe and multiaxial screw for insertion into a single vertebrae.
Figure 7A:
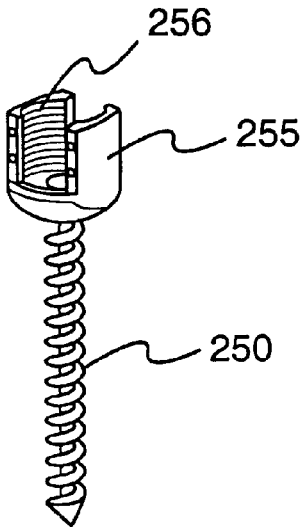
FIG. 7A is a diagram of the screw of FIG. 7.
Figure 8:
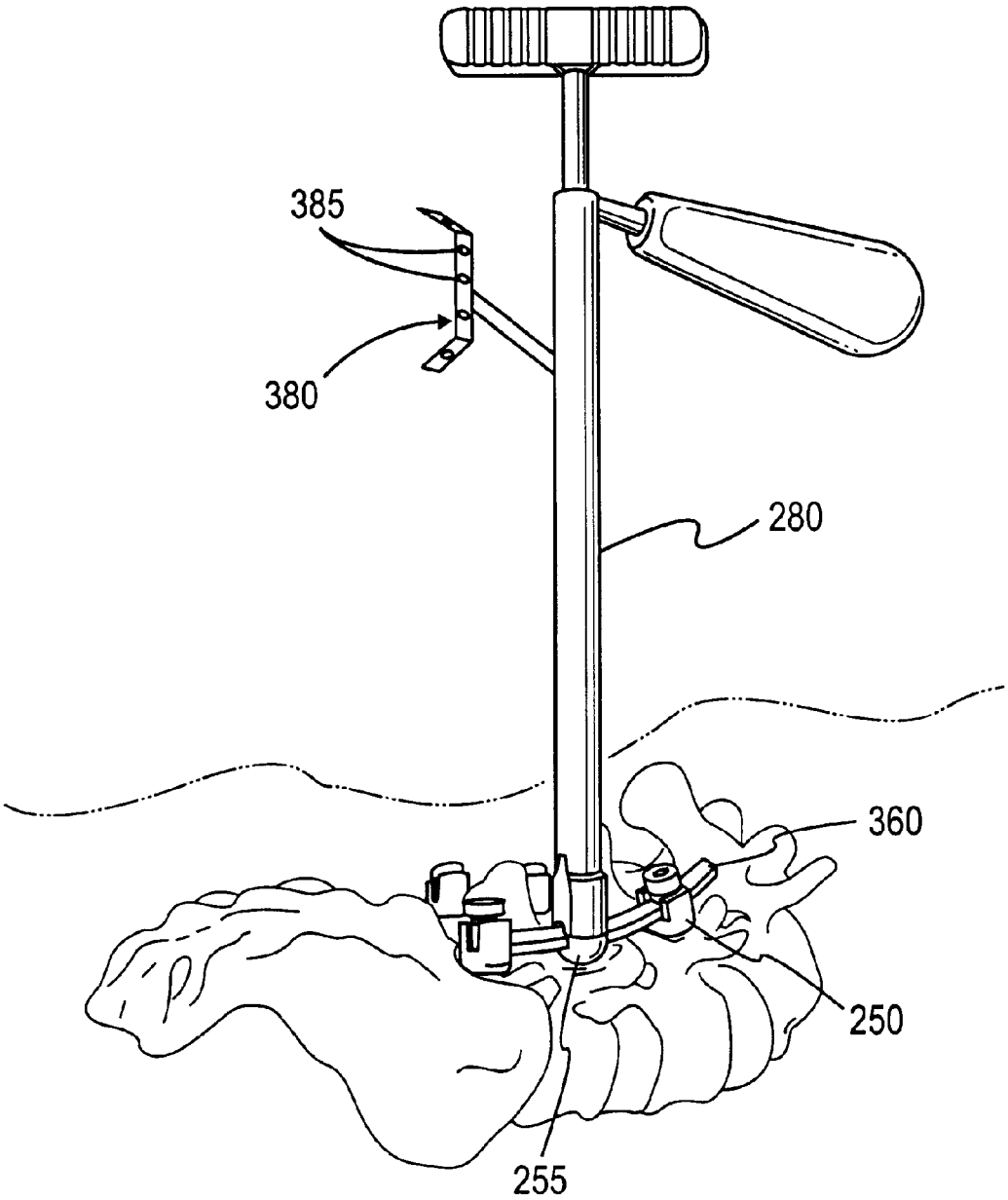
FIG. 8 is a diagram of a head positioning probe, multiaxial screw and spinal segment.

For example, as depicted in FIG. 1, and in more detail FIG. 1A, additional screws 250 or rigid and pointed wires 260 are placed in the vertebrae adjacent to the vertebrae containing the clamp 30 and post 150 prior to scanning. On the image 105 provided by monitor 106, the surgeon can see the clamp 30 or screw 42 and fiducial array 170 and also the additional screws 250, wires 260 or other imageable devices. When screws 250 or other devices are used, these screws 250 (as depicted in FIG. 7) may contain a divot 256 or other specially shaped interface on the head 255 so that a pointer probe 130 can be used to point to the head 255 of the screw 250 (or wire) and indicate the orientation of the screw 250 or wire 260 to the surgical navigation system by communicating to the controller 114 or by emission from LEDs 195 on probe 130 to digitizer 110. The image of these additional screws 250 also appear in the scan. Once the patient is then moved to the operating facility, rather than the scanning area, the image of the screw 250 can be compared to the actual position of the screw 250 as indicated by the pointer probe 130 that is touched to the head 255 of the screw 250 or wire 260. If necessary, the operator can manipulate the position of the patient to move the spinal element and thus the location of the screw 250 or wire 260 to realign the spinal elements with the earlier image of the spine. Alternatively, the operator can manipulate the image to correspond to the current position of the spinal segments.

For additional positioning information, the operator can place additional rigid wires 260 or screws 250 into the vertebrae, for example, located at the superior (toward the patient's head) and inferior (towards the patient's feet) ends of the spinal process to more accurately position those vertebrae relative to the other vertebrae and the image data. Additionally, the wires 260 and screws 250 implanted to provide positioning information can also be equipped with emitters, such as, for example, LEDs, to provide additional information to the surgical navigation system on the location of the wire 260 or screw 250, and thus the vertebra to which they are affixed.

Alternatively, the patient can be placed in a position stabilizing device, such as a spinal surgery frame 125 or board, before a scan is taken, and then moved to the operating facility for the procedure, maintaining the spine segments in the same position from the time of scanning until the time of surgery. Alternatively, a fluoroscope can be used to reposition the spinal segments relative to the earlier image from the scan. An ultrasound probe can be used to take real-time images of the spinal segment which can be portrayed by monitor 106 overlayed or superimposed on image 105. Then the operator can manually manipulate the spinal elements and take additional images of these elements with the fluoroscope to, in an iterative fashion, align the spinal elements with the previously scanned image 105.

Alternatively, a clamp 30 or screw 42 and superstructure 20 can be rigidly fixed to each vertebra involved in the surgical or medical procedure to register the position of each vertebra as explained previously for a single vertebra:

After the spinal elements are registered in the spine, various medical and surgical procedures can be performed on that patient. For example, spinal implants, endoscopes, or biopsy probes can be passed into the spine and procedures such as, for example, spinal fusion, manipulation, or disc removal can be performed percutaneously and facilitated by the surgical navigation image-guiding system. Additionally, a radiation dose can be targeted to a specific region of the vertebrae.

Figure 9:
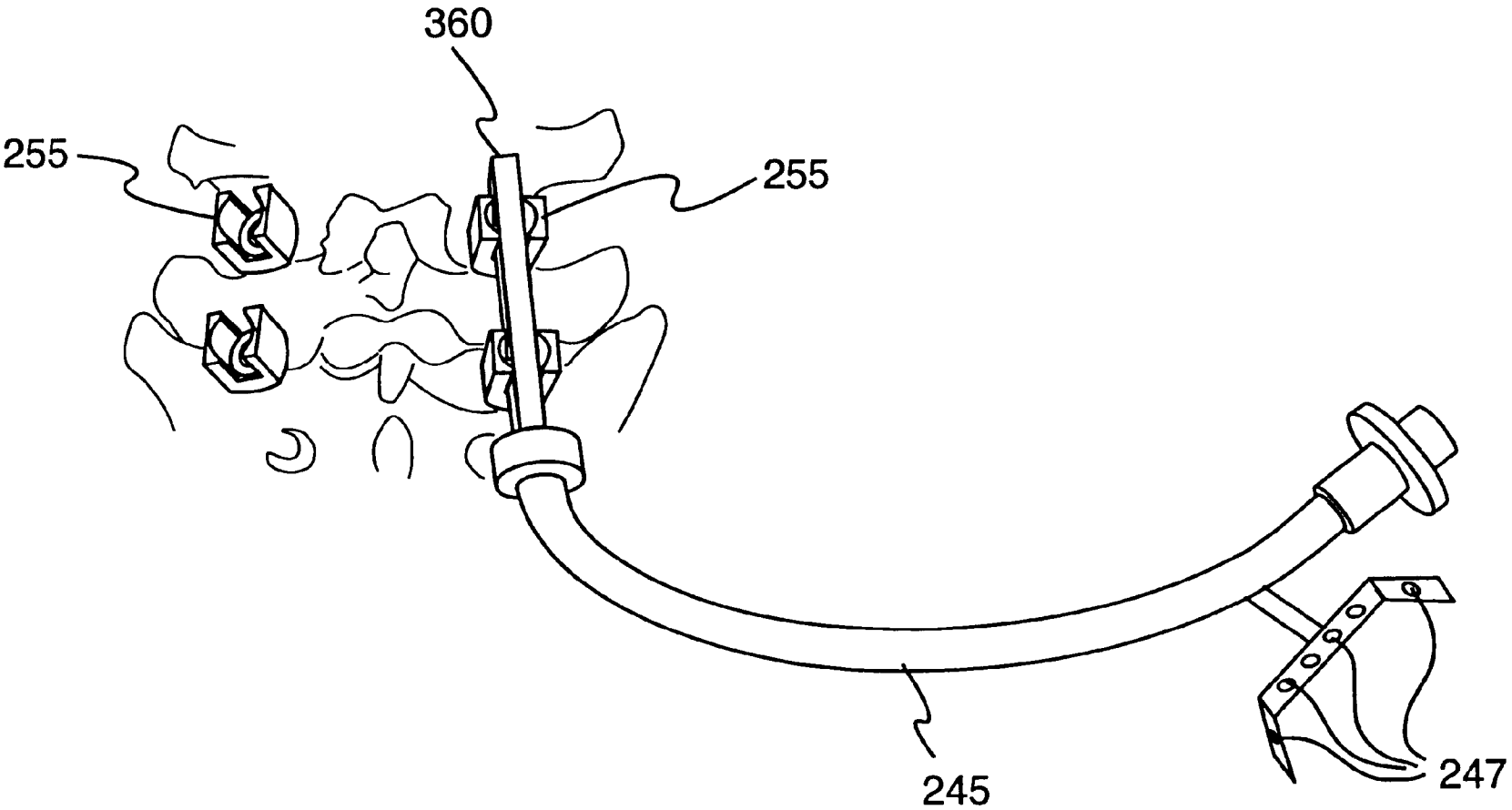
FIG. 9 is a diagram of a rod inserter with an LED.
Figure 12:
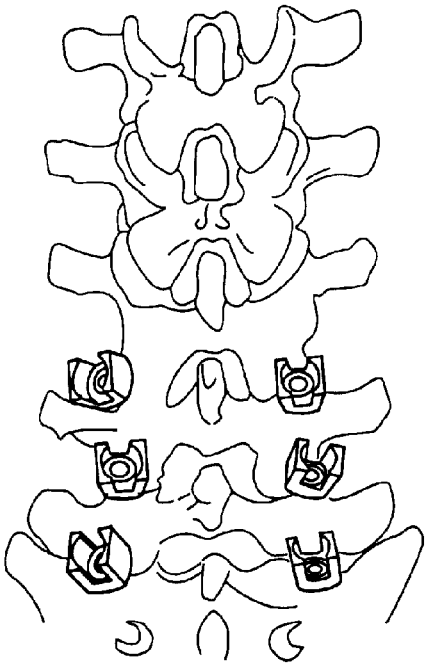
FIG. 12 is a posterior view of spinal segment and implanted screws before alignment.
Figure 13:
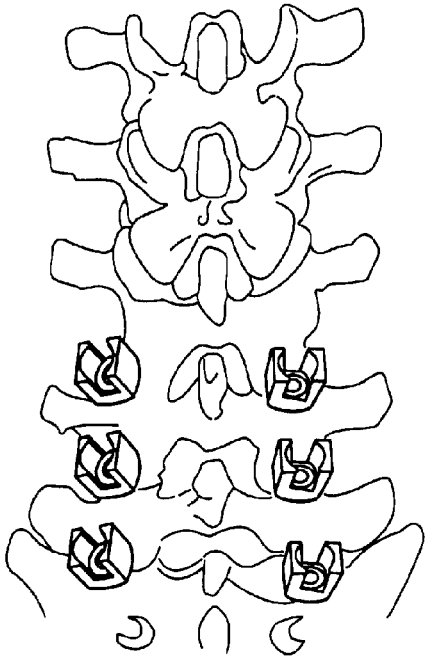
FIG. 13 is a posterior view of spinal segment and implanted screws after alignment.

One such procedure facilitated by the apparatus and methods described above is the percutaneous insertion of screws and rods, fixed to different vertebra in a spine to stabilize them. Once screws, for example multiaxial screws 250, (as depicted in FIG. 12, before manipulation) are implanted through small incisions they can be manipulated by a head-positioning probe 280. The final position of screws 250 and heads 255 are depicted in FIG. 13. This probe 280, as depicted in FIG. 7, includes a head 285 that mates in a geometrically unique fashion with the head 255 of the screw 250. An emitter, such as for example an LED array 380 on the probe 280, indicates the location and orientation of the screw head 255 to the computer 114 of the surgical navigation system by providing an optical signal received by digitizer 110. The screw head 255 can then be rotatably manipulated under the patient's skin by the head positioning probe 280 to be properly oriented for the receipt of a rod 360 inserted through the rotating head 255. The operator can then plan a path from the head 255 of each screw 250 to the other screws 250 to be connected. Then, with reference now to FIG. 9, an optically tracked rod inserter 245 also equipped with emitters, such as, for example LEDs 247, can be placed through another small incision to mate with and guide a rod 360 through the holes or slots in the screw heads 245, through and beneath various tissues of the patient, with the rod inserter 245, and, therefore, the rod 360, fixed to the inserter 245, being tracked in the surgical navigation system. The operator can also use the computer 114 to determine the required bending angles of the rod 360. For greater visualization, the geometry of the screws 250 could be loaded into the computer 114 and when the position and orientation of the head 255 is given to the computer 114 via the probe 280, the computer 114 could place this geometry onto the image data and three-dimensional model. The rod 360 geometry could also be loaded into the computer 114 and could be visible and shown in real time on monitor 106 as the operator is placing it in the screw heads 255.

In an alternative procedure, one or more plates and/or one or more wires may be inserted instead of one or more rods 360.

It will be apparent to those skilled in the art that various modifications and variations can be made in the present invention and in construction of this surgical navigation system without departing from the scope or spirit of the invention. Other embodiments of the invention will be apparent to those skilled in the art from consideration of the specification and practice of the invention disclosed herein. It is intended that the specification and examples be considered as exemplary only.

What is claimed is:

[1. An apparatus for facilitating percutaneous placement of surgical instruments into the spine, adapted for use with a surgical navigation system employing an energy-detecting array in communication with a surgical navigation computer to track positions of instruments in three dimensional space relative to a known reference point, said apparatus comprising:

a connector adapted to be rigidly attached to a portion of the spine;

at least one central post connected to said connector;

a position identification structure rigidly and removably connected to said central post at a predetermined position on said central post and adapted to be reconnected at the same said predetermined position, said identification structure being further adapted to allow a patient to be scanned with the structure connected to the central post, said structure including an assembly for communicating positioning information with respect to said assembly to the energy detecting array and surgical navigation computer; and a connector assembly for said reconnecting of said structure substantially to said predetermined position on said central post.]

[2. The apparatus of claim 1, wherein the connector is a clamp having teeth adapted for biting into a spinous process.]

[3. The apparatus of claim 1, wherein the connector includes an elongated fixture with a central axis and a threaded end adapted to be inserted into the spinous process and a substantially rigid wire connected to the fixture with the central axis of the wire adapted to be implanted into the spinous process at an angle to elongated fixture to prevent the fixture from rotating.]

[4. The apparatus of claim 1, wherein said assembly for communication positioning information is a substantially H-shaped frame.]

[5. The apparatus of claim 1, wherein said assembly for communicating positioning information is a substantially W-shaped frame.]

[6. The apparatus of claim 1, wherein said assembly for communicating positioning information is a substantially U-shaped frame.]

[7. The apparatus of claim 1, wherein said assembly for communicating positioning information is a substantially X-shaped frame.]

[8. The apparatus of claim 1, wherein said assembly for communicating positioning information comprises:

a fiducial array for registering the location of a spinal element with rigidly connected fiducials; and a reference arc for signaling the position of a spinal element, said arc further comprising rigidly connected emitters.]

[9. The apparatus of claim 1, wherein said reference point is on the spine.]

[10. A method for monitoring the location of an instrument, surgical implant and various portions of the body, to be operated on, using a surgical navigation system with a surgical navigation computer and a digitizer array for monitoring the location of instruments in three-dimensional space relative to a known reference point, said method comprising the steps of:

attaching a fixture having a central post to a portion of the spine;

removably attaching an identification structure including a fiducial array and a reference arc to said central post;

providing a scanned three-dimensional image of a patient including said fiducial array rigidly attached to said central post of said fixture, said fixture being rigidly attached to the patient to identify the position of said fixture and said fiducial array on the scanned image;

using an image-guided system, by touching an image guided surgical pointer to one or more fiducials on the fiducial array to register the location of a spinal element fixed to said array; and emitting a signal from said reference arc to indicate changes in position of the spinal element during a surgical procedure.]

[11. The method of claim 10, further comprising:

performing a surgical procedure percutaneously on a patient using an instrument and implant locatable relative to the spinal element and said structure in known positions identified in the surgical navigation system.]

[12. The method of claim 10, further comprising:

inserting a threaded fixture having a substantially rigid wire into a spinal element; and touching an image guided pointer to said threaded fixture and wire to positively register the location of said fixture and wire in a surgical navigation computer.]

[13. The method of claim 10, further comprising:

implanting imageable devices into spinal elements to identify the location of the spinal elements in the surgical navigation computer.]

[14. The method of claim 10, further comprising:

implanting imageable devices into a plurality of spinal elements; and manipulating the patient's spine by viewing the location of the implanted devices, as communicated to the surgical navigation computer by touching an instrument with a tracking emitter to said implanted imageable devices to align the actual position of the spinal elements with the previously scanned image.]

[15. The method of claim 10 further comprising:

percutaneously implanting screws into spinal elements; and locating the position of said screws using image guided surgical navigation techniques. ]

[16. The method of claim 15 further comprising:

manipulating the orientation of the screw heads percutaneously using a head-positioning probe for communicating location containing an emitter, said probe communicating to the surgical navigation computer the orientation of the screw heads; and using a head positioning tool for manipulating implants having an end portion that mates with the heads of the screws and rotating the screws to receive a connecting implant.]

[17. The method of claim 16 further comprising:

tracking the location and position of the connecting implant by means of an instrument affixed to the implant having emitters capable of communicating orientation and location to the surgical navigation computer.]

[18. A system for use in performing the percutaneous placement of surgical implants and instruments into the spine using image guided surgery and a surgical navigation computer and energy detecting array, said system comprising:

means for attaching a fixture to a portion of the spine;

means for communicating position information to the surgical navigation computer and energy detecting array said means rigidly and removably connected to said means for attaching a fixture;

means for providing location information of said spinal portion to the surgical navigation system adapted to be connected to spinal elements;

means for indicating screw-head position said means electrically connected to the surgical navigation system and adapted to mate with the head of a screw implanted in one or more of said spinal elements.]

[19. The system of claim 18 further comprising:

an elongated implant adapted to be inserted into said implanted screws;

means for indicating the position of said elongated implant electrically connected to the surgical navigation system and adapted to mate with the elongated implant.]

[20. The system of claim 18, wherein said implanted screws have heads and the elongated implant is a rod adapted to be guided through holes in said implanted screw heads. ]

*21. A method of registering a physical space defined relative to a subject to an image space of the subject, comprising:*

*connecting an attaching device to the subject;*

*connecting at least one of a fiducial portion or a reference portion to the connected attaching device with a connector in a geometric orientation and location;*

*acquiring image data of the subject and the connected at least one fiducial portion or reference portion that is connected to the subject in the geometric orientation and location;*

*removing the connected at least one fiducial portion or reference portion from the connected at least one clamp or screw after acquiring the image data; and*

*registering the physical space of the subject to the image space of the acquired image data, including:*

*reattaching at least one of the fiducial portion or the reference portion to the connected attaching device in the geometric orientation and location as during the acquiring the image data, and*

*determining a location of a registration portion of the connected at least one fiducial portion or reference portion.*

*22. The method of claim 21, further comprising:*

*attaching the reference portion to the connected attaching device after acquiring the image data of the subject.*

*23. The method of claim 21, wherein determining the location of the registration portion of the fiducial portion includes determining a location of at least one divot on the fiducial portion.*

*24. The method of claim 23, further comprising:*

*folding the fiducial portion to reduce a volume encompassed by the fiducial portion.*

*25. The method of claim 23, further comprising:*

*removing the fiducial portion subsequent to the registering the subject space to the image space and maintaining registration of the subject space to the image space with the attached reference portion.*

*26. The method of claim 23, wherein determining a location of at least one divot on the fiducial portion includes tracking an instrument to touch the at least one divot.*

*27. The method of claim 21, wherein connecting the attaching device to the subject includes fixing a clamp to the subject by moving a first arm and a second arm towards one another to compress a structure of the subject between the first arm and the second arm to hold the clamp relative to the structure.*

*28. A method of registering a physical space defined relative to a subject to an image space of the subject, comprising:*

*connecting a device to the subject;*

*connecting at least a portion of a super-structure to the connected device with a connector;*

*acquiring image data of the subject and the connected at least a portion of the super-structure connected to the device that is connected to the subject;*

*removing the connected at least a portion of the super-structure from the connected device after acquiring the image data; and*

*registering the physical space of the subject to the image space of the acquired image data, including:*

*re-connecting the at least the portion of the super-structure to the connected device in a same geometric orientation and location as during the acquiring the image data, and*

*determining a location of a registration portion of the re-connected at least a portion of the super-structure.*

*29. The method of claim 28, wherein connecting the device to the subject includes fixing at least one of a clamp or a screw to a structure of the subject.*

*30. The method of claim 28, wherein connecting at least the portion of the super-structure to the connected device includes connecting at least one of a fiducial portion or a reference arc to the fixed device with a connector to the device.*

*31. The method of claim 28, wherein connecting the device to the subject includes fixing the device to a structure of the subject.*

*32. The method of claim 31, wherein connecting at least the portion of the super-structure to the device includes connecting a reference portion to the connected device after acquiring the image data of the subject.*

*33. The method of claim 28, wherein determining the location of the registration portion of the re-connected at least a portion of the super-structure includes determining a location of a plurality of divots on the at least a portion of the super-structure.*

*34. The method of claim 33, wherein re-connecting the at least the portion of the super-structure includes re-connecting at least a fiducial portion that defines the plurality of divots.*

*35. The method of claim 34, further comprising:*

*folding the fiducial portion to reduce a volume encompassed by the fiducial portion.*

*36. The method of claim 34, further comprising:*

*removing the fiducial portion subsequent to the registering the physical space to the image space and maintaining registration of the physical space to the image space via the re-connected at least a portion of the super-structure.*

*37. The method of claim 36, wherein re-connecting the at least the portion of the super-structure includes connecting at least a reference portion;*

*wherein maintaining registration of the physical space to the image space includes tracking the connected reference portion.*

*38. The method of claim 28, wherein connecting the device to the subject includes connecting a clamp to a structure of the subject by at least moving a first arm towards a second arm to compress the structure between the first arm and the second arm to hold the clamp relative to the structure.*

*39. A system for registering a physical space defined relative to a subject to an image space of the subject, comprising:*

*a device operable to be connected to the subject; and*

*at least one of a reference portion operable to be detachably connected to the device or a fiducial portion operable to be detachably connected to the device;*

*wherein the reference portion is operable to determine a location of the subject and the fiducial portion is operable to be registered relative to an image of the subject.*

*40. The system of claim 39, further comprising:*

*a member extending and detachable from the device.*

*41. The system of claim 40, wherein the device includes a screw operable to be driven into the subject;*

*wherein the member is detachable from the screw.*

*42. The system of claim 40, wherein the device includes a clamp operable to compress a structure of the subject between a first arm and a second arm;*

*wherein the member is detachable from the clamp.*

*43. The apparatus of claim 40, further comprising:*

*a connector to interconnect the at least one of the reference portion or the fiducial portion to the member;*

*wherein the member extends from a first end to a second end, wherein one of the first end or the second end of the member is operable to be connected to the device;*

*wherein the connector is connected near the second end;*

*wherein the connector is operable to interconnect the reference portion and the member.*

*44. The apparatus of claim 43, wherein the connector includes a shaped interface such that the reference portion and the member can be separated and placed back in the same geometric orientation and location.*

*45. The apparatus of claim 39, wherein the fiducial portion includes a plurality of divots operable to be registered to increase accuracy when compared to a single registration divot.*

* * * * *